US008354372B2

(12) United States Patent
Clark et al.

(10) Patent No.: US 8,354,372 B2
(45) Date of Patent: Jan. 15, 2013

(54) CYCLISED ALPHA-CONOTOXIN PEPTIDES

(75) Inventors: Richard Clark, Chapel Hill (AU);
David James Craik, Chapel Hill (AU)

(73) Assignee: The University of Queensland (AU)

( * ) Notice: Subject to any disclaimer, the term of this patent is extended or adjusted under 35 U.S.C. 154(b) by 724 days.

(21) Appl. No.: 12/297,110

(22) PCT Filed: Apr. 3, 2007

(86) PCT No.: PCT/AU2007/000439
§ 371 (c)(1),
(2), (4) Date: Apr. 20, 2009

(87) PCT Pub. No.: WO2007/118270
PCT Pub. Date: Oct. 25, 2007

(65) Prior Publication Data
US 2010/0120670 A1    May 13, 2010

(30) Foreign Application Priority Data

Apr. 13, 2006  (AU) ............................... 2006901976
Nov. 15, 2006  (AU) ............................... 2006236006

(51) Int. Cl.
*A61K 38/00*  (2006.01)
*A61K 38/16*  (2006.01)
*A61K 38/12*  (2006.01)
*C07K 5/00*   (2006.01)
*C07K 7/00*   (2006.01)
*C07K 16/00*  (2006.01)
*C07K 17/00*  (2006.01)

(52) U.S. Cl. ......................... 514/1.1; 514/17.4; 530/317
(58) Field of Classification Search ........................ None
See application file for complete search history.

(56) References Cited

U.S. PATENT DOCUMENTS

| | | | | |
|---|---|---|---|---|
| 5,464,633 | A * | 11/1995 | Conte et al. | 424/480 |
| 5,614,219 | A * | 3/1997 | Wunderlich et al. | 424/472 |
| 5,866,682 | A | 2/1999 | McIntosh et al. | |
| 6,153,219 | A * | 11/2000 | Creeth et al. | 424/451 |
| 6,352,974 | B1 * | 3/2002 | Ghirri et al. | 424/456 |
| 7,001,883 | B1 * | 2/2006 | Craik et al. | 514/17.4 |
| 7,312,195 | B2 * | 12/2007 | Craik et al. | 514/18.1 |
| 7,316,819 | B2 * | 1/2008 | Crotts et al. | 424/464 |
| 2005/0256301 | A1 | 11/2005 | Craik et al. | |

FOREIGN PATENT DOCUMENTS

| | | |
|---|---|---|
| WO | WO 98/51322 A1 | 11/1998 |
| WO | WO 00/15654 A1 | 3/2000 |
| WO | WO 02/079236 A1 | 10/2002 |
| WO | WO 2007/014432 A1 | 2/2007 |

OTHER PUBLICATIONS

Cartier et al. A New alpha-Conotoxin Which Targets alpha3beta2 Nicotinic Acetylcholine Receptors. JBC, 1996, vol. 271, No. 13, pp. 7522-7528.*
Nicke et al. Isolation, Structure, and Activity of GID, a Novel alpha4/7-Conotoxin with an Extended N-terminal Sequence. JBC, 2003, vol. 278, No. 5, pp. 3137-3144.*
Nicke et al. Isolation, Structure, and Activity of GID, a novel alpha-4/7-Conotoxin with an Extended N-terminal Sequence. JBC, 2003. vol. 278, No. 5, pp. 3137-3144.*
Clark et al., "Engineering stable peptide toxins by means of backbone cyclization: Stablization of the α-conotoxin MII" Proceedings of the National Academy of Sciences, Sep. 27, 2005, 102(39), 13767-13772.
Bax, A. et al., "MLEV-17-Based Two-Dimensional Homonuclear Magnetization Transfer Spectroscopy," J. Magn. Reson., 1985, 65, 355-360.
Brünger, A.T. et al., "New Applications of Simulated Annealing in X-Ray Crystallography and Solution NMR," Structure, 1997, 5(3), 325-336.
Camarero, J.A. et al., "Fmoc-Based Synthesis of Peptide r-Thioesters Using an Aryl Hydrazine Support," J. Org. Chem., 2004, 69, 4145-4151.
Clark R. et al., "The Synthesis, Structural Characterization, and Receptor Specificity of the α-Conotoxin Vc1.1," J. Biol. Chem.., 2006, 281(32), 23254-23263.
Clippingdale, A.B. et al., "Peptide Thioester Preparation by Fmoc Solid Phase Peptide Synthesis for Use in Native Chemical Ligation," J. Pept. Sci., 2000, 6, 225-234.
Dawson P. et al., "Synthesis of Proteins by Native Chemical Ligation," Science, 1994, 266, 776-779.
Dawson, P. et al., "Synthesis of Peptides and Proteins without Cysteine Residues by Native Chemical Ligation Combined with Desulfurization," J. Am. Chem. Soc., 2001, 123(4), 526-533.
Eccles, C. et al., "Efficient analysis of protein 2D NMR spectra using the software package EASY," J. Biomol. NMR, 1991, 1, 111-130.
Göransson, U. et al., "Disulfide Mapping of the Cyclotide Kalata B1," J. Biol. Chem., 2003, 278(48), 48188-48196.
Griesinger, C. et al., "Practical Aspects of the E.COSY Technique. Measurement of Scalar Spin-Spin Coupling Constants in Peptides," J. Magn. Reson., 1987, 75, 474-492.
Güntert, P. et al., "Torsion Angle Dynamics for NMR Structure Calculation with the New Program DYANA," J. Mol. Biol., 1997, 273, 283-298.
Hogg R. et al., "Single Amino Acid Substitutions in .-Conotoxin PnIA Shift Selectivity for Subtypes of the Mammalian Neuronal Nicotinic Acetylcholine Receptor," J. Biol. Chem, 1999, 274(51), 36559-36564.
Hogg R. et al., "Nicotinic acetylcholine receptors: from structure to brain function," Review of Physiology, Biochemistry and Pharmacology, 2003, 147, 1-46.
Hutchinson, E.G. et al., "PROMOTIF—A program to identify and analyze structural motifs in proteins," Protein Sci., 1996, 5, 212-220.
Craik, D., IDrugs, 15th World Congress on Animal, Plant and Microbial Toxins, 2006, 9(10), 679-681.

(Continued)

*Primary Examiner* — Marcela M Cordero Garcia
(74) *Attorney, Agent, or Firm* — Woodcock Washburn LLP

(57) ABSTRACT

This invention relates to an oral or enteral pharmaceutical preparation comprising at least one synthetically cyclised alpha-conotoxin peptide having an amide cyclised backbone such that the peptide has no free N- or C-terminus, said peptide having the ability to inhibit a nicotinic acetylcholine receptor and comprising four cysteine residues bonded in pairs to form two disulfide bonds, wherein the N-terminus of the corresponding linear/non-cyclised conotoxin peptide is linked to the C-terminus by a peptide linker, in a vehicle which is pharmaceutically suitable for oral or enteral administration.

15 Claims, 12 Drawing Sheets

OTHER PUBLICATIONS

Ingenito, R. et al., "Solid Phase Synthesis of Peptide C-Terminal Thioesters by Fmoc/t-Bu Chemistry," J. Am. Chem. Soc., 1999, 121, 11369-11374.

Jeener, J. et al., "Investigation of exchange processes by two-dimensional NMR spectroscopy," J. Chem. Phys., 1979, 71(11), 4546-4553.

Kumar, A. et al., "A Two-Dimensional Nuclear Overhauser Enhancement (2D NOE) Experiment for the Elucidation of Complete Proton-Proton Cross-Relaxation Networks in Biological Macromolecules," Biochem. Biophys. Res. Commun., 1980, 95(1), 1-6.

Lang P.M. et al., "Characterization of Neuronal Nicotinic Acetylcholine Receptors in the Membrane of Unmyelinated Human C-Fiber Axons by In Vitro Studies," J. Neurophysiol., 2003, 90, 3295-3303.

Lang P.M. et al., "A conus peptide blocks nicotinic receptors of unmyelinated axons in human nerves," Neuroreport, 2005, 16(5), 479-483.

Laskowski, R.A. et al., "AQUA and PROCHECK-NMR: Programs for checking the quality of protein structures solved by NMR," J. Biomol. NMR, 1996, 8, 477-486.

Lawrence, G.W. et al., "Botulinum A and the light chain of tetanus toxins inhibit distinct stages of Mg • ATP-dependant catecholamine exocytosis from permeabilised chromaffin cells," Eur. J. Biochem., 1994, 222, 325-333.

Linge, J.P. et al., "Influence of non-bonded parameters on the quality of NMR structures: A new force field for NMR structure calculation," J. Biolmol. NMR, 1999, 13, 51-59.

Lloyd, G. et al., "Neuronal Nicotinic Acetylcholine Receptors as Novel Drug Targets," J. Pharmacol. Exp. Ther., 2000, 292(2), 461-467.

Metabolic website dated Apr. 2005, "ACV1—A Novel Therapeutic for Neuropathic Pain: Technical Summary of Preclinical Data," 1-16.

Meunier, F.A. et al., "Glycerotoxin from *Glycera convolute* stimulates neurosecretion by up-regulating N-type $Ca^{2+}$ channel activity," EMBO J., 2002, 21(24), 6733-6743.

Meunier, F.A. et al., "Trachynilysin mediates SNARE-dependent release of catecholamines from chromaffin cells via external and stored $Ca^{2+}$," J. Cell Sci., 2000, 113 (Pt 7), 1119-1125.

Piotto, M. et al., "Gradient-tailored excitation for single-quantum NMR spectroscopy of aqueous solutions," J. Biomol. NMR, 1992, 2, 661-665.

Rance, M. et al., "Improved Spectral Resolution in COSY $^1$H NMR Spectra of Proteins Via Double Quantum Filtering," Biochem. Biophys. Res. Commun., 1983, 117(2), 479-485.

Sandall, D.W. et al., "A Novel R-Conotoxin Indentified by Gene Sequencing Is Active in Suppressing the Vascular Response to Selective Stimulation of Sensory Nerves in Vivo," Biochem., 2003, 42(22), 6904-6911.

Satkunanathan, N. et al., "Alpha-conotoxin Vc1.1 alleviates neuropathic pain and accelerates functional recovery of injured neurones," Brain Research, 2005, 1059(2), 149-158.

Schnölzer, M. et al., "In Situ Neutralization in Bio-chemistry Solid Phase Peptide Synthesis," Int. J. Pept. Protein Res., 2007, 13(1-2), 31-44.

Shin, Y. et al., "Fmoc-Based Synthesis of Peptide-$^R$Thioesters: Application to the Total Chemical Synthesis of a Glycoprotein by Native Chemical Ligation," J. Am. Chem. Soc., 1999, 121, 11684-11689.

Tam, J.P. et al., "Thia Zip Reaction for Synthesis of Large Cyclic Peptides: Mechanisms and Applications," J. Am. Chem. Soc., 1999, 121, 4316-4324.

Vincler, M. et al., "Molecular mechanism for analgesia involving specific antagonism of $\alpha 9\alpha 10$ nicotinic acetylcholine receptors," PNAS, 2006, 103(47), 17880-17884.

Wüthrich, K., "Sequence-Specific Resonance Assignments in Proteins," NMR of Proteins and Nucleic Acids, New York: Wiley, 1986, 130-161.

\* cited by examiner

CYCLISED ALPHA-CONOTOXIN PEPTIDES

CROSS-REFERENCE TO RELATED APPLICATIONS

This application is the national stage of PCT/AU2007/000439, filed Apr. 3, 2007, which claims the benefit of priority to Australian Application No. 2006901976, filed Apr. 13, 2006, and Australian Application No. 2006236006, filed Nov. 15, 2006, the entire contents of each of which are hereby incorporated by reference in their entirety.

BACKGROUND OF THE INVENTION

This invention relates to α-conotoxin peptides, and in particular to cyclised α-conotoxin peptides useful in the therapeutic treatment of humans. The invention especially relates to oral and enteral preparations comprising these peptides, the use of these peptides in the manufacture of pharmaceutical preparations, and the use of these pharmaceutical preparations in the prophylaxis or treatment of conditions or diseases in humans.

The marine snails of the genus *Conus* (cone snails) use a sophisticated biochemical strategy to capture their prey. As predators of either fish, worms or other molluscs, the cone snails inject their prey with venom containing a cocktail of small bioactive peptides. These toxin molecules, which are referred to as conotoxins, interfere with neurotransmission by targeting a variety of ion-channels or receptors. They typically contain 12-30 amino acids arranged in linear sequence. The venom from any single *Conus* species may contain more than 100 different peptides. The conotoxins are divided into classes on the basis of their physiological targets. For example, the α-conotoxin and Ψ-conotoxins target nicotinic ACh receptors, causing ganglionic and neuromuscular blockade, while the ω-conotoxin class of peptides target voltage-sensitive $Ca^{2+}$-channels, inhibiting neurotransmitter release.

Most conotoxin peptides contain either four (4) or six (6) cysteine residues which are bonded in pairs to form either two (2) or three (3) disulfide bonds respectively, although there are some examples having two cysteine residues bonded to form a single disulfide bond (i.e., conoptessins), as well as some having greater than three disulfide bonds, and others that contain no cysteine residues or disulfide bonds. The peptides of some of the "activity" classes described above share a structural motif, possessing the same number of cysteine residues and the same disulfide bond connectivity. For this reason a new "superfamily" classification system has been developed. For example, the ω-conotoxins and members of the δ and μ-conotoxin classes have six cysteine residues which are bonded in pairs to form three disulfide bonds between cysteine residues I and IV, II and V, and III and VI, where the six Roman numerals represent the six cysteine residues numbering from the N-terminus. Conotoxin peptides having this structural motif belong to the O-superfamily and M-superfamily of conotoxins. Similarly, ρ-conotoxins and most α-conotoxins have four cysteine residues bonded in pairs to form two disulfide bonds between cysteine residues I and III, and II and IV. These conotoxin peptides belong to the "A-superfamily" of conotoxins. The present invention relates to α-conotoxins in the A-superfamily, i.e. α-conotoxin peptides having two disulfide bonds formed between cysteine residues I and III, and II and IV. As indicated above, conotoxin peptides bind to a range of different ion channel receptors in mammals and accordingly they have several potential therapeutic applications, including pain relief in humans. However, in general peptides have several difficulties associated with their use as drugs, including generally poor bioavailability; susceptibility to cleavage by proteases, and unwanted side effects.

One ω-conotoxin, MVIIA (also known as SNX-111, Ziconitide and Prialt), recently received approval by the United States Food and Drug Administration for the treatment of intractable pain associated with cancer, AIDS and neuropathies. The route of administration is currently restricted to intrathecal infusion into the spinal cord because of some of the abovementioned difficulties, and because the receptors targetted by this drug are located within the CNS.

Another ω-conotoxin which has commenced clinical trials is CVID (AM336—Zenyth Pharmaceuticals) which is reported to have improved selectivity for N-type calcium channels over P/Q-type channels relative to Ziconitide. However, even with improved selectivity for particular receptors/channels, conotoxins of the ω class have still been associated with undesirable side effects in some patients. Two other conotoxin peptides (CGX-1160 and CGX-1007 isolated from *Conus geographus*) are also undergoing clinical trials, however administration of these peptides is also restricted to the intrathecal route. Another peptide being investigated for pain is a conotoxin of the χ-class (Xen 2174-Xenome Ltd). Again, administration of this peptide is limited to the intrathecal route.

The main disadvantages of intrathecal or spinal administration of drugs are that administration must be carried out by a doctor or nurse, and for long term treatment a mechanical delivery system and spinal catheter are preferably inserted into the spine of a patient. Hence, such treatment is usually reserved for the terminally ill and/or hospital-bound patients.

The α-conotoxins are a sub-family of conotoxins that typically range in size from 12 to 16 amino acids, and usually have an amidated C-terminus. The α-conotoxins are known to inhibit nicotinic acetylcholine receptors. The α-conotoxins interact with both muscle and neuronal nicotinic acetylcholine receptors (nAChRs) which have been implicated in a range of disorders including Alzheimer's disease, schizophrenia, depression and small cell lung carcinoma, as well as playing a role in analgesia and addiction. α-conotoxin peptides and their potential uses are widely described in the literature (see Lloyd and Williams, 2000, J Pharmacol Exp Ther 292 (2) 461).

The number of residues between the cysteine residues is used to distinguish different classes of α-conotoxins. Based on the number of residues between the second and third cysteine residues (loop 1) and the third and fourth residues (loop 2) they are divided into α3/5, α4/3, α4/4, α4/6 and α4/7 structural subfamilies. Two examples of α-conotoxin peptides having 4/7 loop arrangement are MII and Vc1.1 (also known as ACV1—Metabolic Pharmaceuticals Limited). One of the smallest α-conotoxin peptides is IM1 which has a 4/3 loop arrangement.

Several α-conotoxin peptides have been studied to ascertain their selectivity for the various subtypes of nicotinic acetylcholine receptors, and in particular their selectivity for peripheral nAChR subtypes over central subtypes. nAChRs are expressed at low levels throughout the CNS and PNS, but various subtypes have different distributions. The mammalian nAChRs are composed of combinations of subunits. Seven of these subunit types are the major components involved in ligand binding (α2, α3, α4, α6, α7, α9 and α10) while 4 subunit types (α5, β2, β3 and β4) are considered to be structural, imparting functional and pharmacological properties to the receptors. The different subtypes combine in a variety of ways (generally as heterologous pentamers) to form receptors having particular pharmacological and electrophysiological properties. The α3 subunit is considered to be a peripheral subunit (due to its presence in the PNS) while the α7 subunit is considered to be a subunit prevalent in the CNS.

The α-conotoxin Vc1.1 was first discovered using a PCR screen of cDNAs from the venom ducts of *Conus victoriae* (Sandall et al. Biochemistry, 2003, 42, 6904). The cysteine spacing within the sequence of Vc1.1 indicates that it is a member of the 4/7 subclass of α-conotoxins, which includes the extensively studied conotoxins MII, EpI and PnIB. The three dimensional structure of Vc1.1 comprises a small α-helix spanning residues P6 to D11 and is braced by the I-II, III-IV disulfide connectivity seen in other α-conotoxins (Clark et al., J. Biol. Chem. 2006, 281, 23254). In addition to an amidated C-terminus, which is common to most α-conotoxins, it is also possible to postranslationally modify residues Pro6 and Glu14 in linear Vc1.1 to hydroxyproline and γ-carboxyglutamate respectively. This post translationally modified analogue of Vc1.1 is implicated in nerve regeneration but not pain (WO 02/079236).

Linear Vc1.1, an antagonist of neuronal nAChRs in bovine chromaffin cells, has been shown to alleviate neuropathic pain in three rat models of human neuropathic pain and to accelerate the functional recovery of injured neurons (Satkunanathan et al., 2005, Brain Research 1059 (2) 149-158). In addition it has been reported by Livett et al that ACV-1 is effective at alleviating neuropathic pain in an animal model of diabetic neuropathy. In particular, in the streptozotocin-induced diabetic rat model of peripheral neuropath an anti allodynic effect of ACV-1 was observed at doses of 30 and 300 ug/kg within 1 hr of dosing (IDrugs, 15th World Congress on Animal, Plant and Microbial Toxins, 2006 9, 679-681). As an analgesic, Vc1.1 has been reported be more active than Ziconotide (Sandall et al., 2003, Biochemistry, 42, 6904-6911). More recently, Vc1.1 was shown to antagonize the nicotine-induced increase in axonal excitability of unmyelinated C-fiber axons in isolated segments of peripheral human nerves (Lang et al., 2005, Neuroreport 16, 479-483). As mentioned above neuronal nAChRs are pentameric ligand-gated ion channels composed of combinations of α (α2 to α10) and β (β2 to β4) subunits that are found throughout both the central and peripheral nervous systems. Electrophysiological and immunohistochemical data indicate the functional expression of nAChRs composed of α3, α5 and β4 but not α4, β2 or α7 subunits in axons of unmyelinated C fibers (Lang et al., 2005, Neuroreport 16, 479-483; and Lang et al., 2003, Neurophysiol 90, 3295-3303). Blockade of nAChRs on unmyelinated peripheral nerve fibers may have an analgesic effect on unmyelinated sympathetic and/or sensory axons. Interestingly, synthetic post translationally modified Vc1.1 (ptmVc1.1) was reported to not inhibit the neuronal-type nicotinic response in chromaffin cells and was inactive in two rat neuropathic pain assays. Linear Vc1.1 or ACV1 has commenced phase 2 human clinical trials. Nicotinic agonists have been previously reported to possess analgesic activity. Examples of such nicotinic agonists are epibatadine and ABT-594. It is postulated that these agents act by desensitising the nicotinic receptor, resulting in a reduction of ion flux through the receptor. Under these conditions the agonists are effectively acting as antagonists of the nAChRs and for this reason antagonists of nAChRs have been sought as potential analgesic compounds. Conotoxin peptide Vc1.1 is said to be such an antagonist.

Interestingly, the IC50 values for Vc1.1 at the α3, β4 subtype of the nAchR is in the micromolar range (4.2 µM; Vincler et al., 2006, PNAS, 103, 17881). The analgesic effect of Vc1.1 appears to occur in nanomolar concentrations in vivo.

It has recently been reported that Vc1.1 may produce analgesia through the modulation of α9, α10 nAchRs (Vincler et al., supra). The affinity of Vc1.1 for the α9, α10 nAchR is one hundred fold higher than for the α3, β4 nAchR and falls in the nanomolar range (22.9 nM). Therefore, it appears that one physiological target for Vc1.1 may be the α9, α10 nAchR which is known to have widespread distribution, and located in dorsal root ganglion, neurones, the pituitary, lymphocytes, skin keratinocytes and sperm. However, it is conceivable that there may be other targets yet to be discovered that are responsible for the pain-relieving activity of Vc1.1.

Unlike the previous conotoxin peptides which have been investigated for the treatment of pain and other conditions, Vc1.1 is said to have the advantage that it can be administered subcutaneously or intramuscularly, rather than intrathecally. This is said to provide a significant advantage for Vc1.1 over previous conotoxin peptides, including Ziconitide. However, conotoxin peptide Vc1.1 is said to lack oral bioavailability. According to a document published on Metabolic Pharmaceuticals' website dated January 2006 "ACV1—A novel therapeutic for neuropathic pain, Technical Summary of Preclinical Data" ACV1 is not orally available and current development is as a subcutaneous injectable treatment. Vc1.1 is also reported to be effective in an animal model of inflammatory pain and to accelerate the recovery of injured nerves and tissues.

WO 2007/014432, in the name of Metabolic Pharmaceuticals Limited, describes a method for improving the oral delivery of a peptide drug by linking the C terminal sequence of human growth hormone and analogues of same to the C terminal of the peptide drug. Addition of the C terminal sequence of human growth hormone to a peptide drug allegedly confers oral bioavailability properties to the peptide drug. The patent application describes an orally available peptide that appears to be active in an animal model of neuropathic pain. The peptide comprises Vc1.1 with the amino acid sequence Tyr-Leu-Arg-Ile-Val linked to the C terminus of Vc1.1.

Accordingly, there is still a need for effective method of treating patients with α-conotoxin peptides via oral or enteral routes, particularly in relation to the production of analgesia, the treatment or prevention of neuropathic pain and in the acceleration of recovery from nerve injury.

SUMMARY OF THE INVENTION

The present invention is based on the surprising finding that cyclisation of an α-conotoxin peptide to produce a compound with an amide cyclised backbone gives rise to a cyclised peptide with oral efficacy.

Accordingly in a first aspect the present invention provides an oral or enteral pharmaceutical preparation comprising at least one synthetically cyclised α-conotoxin peptide having an amide cyclised backbone such that the peptide has no free N- or C-terminus, comprising four cysteine residues bonded in pairs to form two disulfide bonds, wherein the N-terminus of the corresponding linear/non-cyclised conotoxin peptide is linked to the C-terminus by a peptide linker, in a vehicle which is pharmaceutically suitable for oral or enteral administration.

Preferably the peptide linker is such that between six and eight natural or unnatural amino acids span the distance between cysteine residues I and IV.

The invention further provides a method for the treatment or prevention of pain comprising the step of orally or enterally administering a pharmaceutical preparation as described above.

In a further embodiment, the invention provides a method for accelerating the recovery of nerve damage comprising the step of orally or enterally administering a pharmaceutical preparation as described above.

The invention further provides a method for the treatment or prevention of Alzheimer's disease, schizophrenia, depression, epilepsy, small cell lung carcinoma, cardiovascular disorders, gastric motility disorders, urinary incontinence, nicotine addiction, mood disorders (such as bipolar disorder, unipolar depression, dysthymia, Tourette Syndrome and seasonal effect disorder) or inflammation comprising the step of orally or enterally administering a pharmaceutical preparation as described above.

In a further embodiment, the invention provides the use of a cyclised α-conotoxin peptide in the manufacture of a medicament for oral or enteral administration for the treatment or prevention of pain or in the acceleration of recovery from nerve damage.

The invention also provides the use of a cyclised α-conotoxin peptide in the manufacture of a medicament for oral or enteral administration for the treatment or prevention of Alzheimer's disease, schizophrenia, depression, epilepsy, small cell lung carcinoma, cardiovascular disorders, gastric motility disorders, urinary incontinence, nicotine addiction, mood disorders (such as bipolar disorder, unipolar depression, Tourette syndrome, dysthymia and seasonal effect disorder) or inflammation.

DESCRIPTION OF PREFERRED EMBODIMENTS

The α-conotoxin class is a very large class of conotoxin peptides with many hundreds of examples being described in the literature. Most of the α-conotoxin peptides are members of the A-superfamily, having four cysteine residues bonded in pairs forming two disulfide bonds between cysteine residues I and III and between cysteine residues II and IV. Some examples of α-conotoxin peptides which have been described in the literature are set out in Table 1 below.

TABLE I

| | | | |
|---|---|---|---|
| Vc1.1 | GCCSDPRCNYDHPEIC | (SEQ ID NO: | 5) |
| Vc1.1ptm | GCCSDORCNYDHPγIC | (SEQ ID NO: | 7) |
| Vg1.1 | DCCSNPPCAHNNPDC | (SEQ ID NO: | 8) |
| An1.1 | GCCSHPACYANNQDYC | (SEQ ID NO: | 9) |
| PreVc1.1 | GCCSDPRCNYDHPEICG | (SEQ ID NO: | 10) |
| SII.4 | GGCCSYPPCNVSYPEIC | (SEQ ID NO: | 11) |
| Di1.1 | GCCSNPPCAHNNPD-CR | (SEQ ID NO: | 12) |
| Om1.1 | GCCSYPPCFATNPD-C | (SEQ ID NO: | 13) |
| Vr1.1 | DCCSNPPCSQNNPD-CM | (SEQ ID NO: | 14) |
| Vr1.2 | DCCSNPPCANHHPD-CR | (SEQ ID NO: | 15) |
| Bt1.4 | GCCSHPACSVNHPELC | (SEQ ID NO: | 16) |
| Da1.1 | GCCSHPACNVDHPEIC | (SEQ ID NO: | 17) |
| TIB | GCCSHPACSGNNPEFCRQ | (SEQ ID NO: | 18) |
| Pn1.1 | GCCSHPPCAMNNPDYC | (SEQ ID NO: | 19) |
| Cr1.2 | GCCSNPVCHVEHPELCRRRR | (SEQ ID NO: | 20) |
| Tx1.2 | GCCSRPPCIANNPDLC | (SEQ ID NO: | 21) |
| Bt1.8 | GGCCSHPACSVTHPELC | (SEQ ID NO: | 22) |
| Lv1.4 | EDCCSDPRCSVGHQDLC | (SEQ ID NO: | 23) |
| Lv1.7 | EDCCSDPRCSVGHQDMC | (SEQ ID NO: | 24) |
| Mr1.4 | GCCSHPACSVNNQDIC | (SEQ ID NO: | 25) |
| O1.7 | GCCSHPPCAQNNQDYC | (SEQ ID NO: | 26) |
| Om1.5 | GCCSDPSCNVNNPDYC | (SEQ ID NO: | 27) |
| Rg1.4 | GCCSHPVCKVRYPDLC | (SEQ ID NO: | 28) |
| Pn1.2 | GCCSHPPCFLNNPDYC | (SEQ ID NO: | 29) |
| Da1.2 | GCCSRPACIANNPDLC | (SEQ ID NO: | 30) |
| EPI | GCCSDPRCNMNNPDYC | (SEQ ID NO: | 31) |
| Pn1A | GCCSLPPCAANNPDYC | (SEQ ID NO: | 32) |
| Pn1B | GCCSLPPCALSNPDYC | (SEQ ID NO: | 33) |
| Au1A | GCCSYPPCFATNSDYC | (SEQ ID NO: | 34) |
| Au1B | GCCSYPPCFATNPD-C | (SEQ ID NO: | 35) |

TABLE I-continued

| | | | |
|---|---|---|---|
| Au1C | GCCSYPPCFATNSGYC | (SEQ ID NO: | 36) |
| MII | GCCSNPVCHLEHSNL | (SEQ ID NO: | 37) |
| PIA | RDPCCSNPVC TVHNPQIC | (SEQ ID NO: | 38) |
| GIC | GCCSHPACFASNPDYC | (SEQ ID NO: | 39) |
| GID | IRDγCCSNPACRVNNOHVC | (SEQ ID NO: | 40) |
| AnIA | CCSHPACAANNQDYC | (SEQ ID NO: | 41) |
| AnIB | GGCCSHPACAANNQDYC | (SEQ ID NO: | 42) |
| AnIC | GGCCSHPACFASNPDYC | (SEQ ID NO: | 43) |
| PeIA | GCCSHPACSVNHPELC | (SEQ ID NO: | 44) |
| BuIA | GCCSTPPCAVLYC | (SEQ ID NO: | 45) |

In the above table γ represents γ-carboxyglutamate and O represents 4-hydroxy proline. The remaining symbols are those commonly used to designate naturally occurring amino acids. Most of the above peptides have an amidated C-terminus.

The cyclisation of conotoxin peptides to improve stability was first described by Craik et al. in International Patent Application No. PCT/AU99/00769 filed on 14 Sep., 1999 (WO 00/15654). Accordingly the cyclised α-conotoxin peptides formulated according to the present invention may be prepared using the methodology described in that patent application, the entire contents of which is incorporated herein by reference.

As used herein, unless the context requires otherwise, the term "linear" when used in connection with a conotoxin peptide means that the peptide is in a non-cyclised state, i.e. the N-terminus and C-terminus have not been linked (directly or with a linker) to form an amide cyclised backbone. Although the presence of one or more disulfide bonds in an α-conotoxin peptide will introduce a degree of circularity to the peptide, a peptide with such a disulfide bond is still to be regarded as "linear" if there is no cyclisation of the backbone of the peptide through linking of the N- and C-termini.

The terms "oral/enteral bioavailability", "orally/enterally administrable", "suitable for oral/enteral administration" and "oral efficacy" as used herein refer to the ability of the cyclised peptide to be administered via the oral or enteral routes to provide a pharmaceutically relevant effect, such as the treatment or prevention of pain, Alzheimer's disease etc. or in the acceleration of recovery from nerve damage. Although the effect is believed to occur through the interaction of the peptide with its postulated target, the term is not intended to impose such a restriction on the scope of this invention. Other or alternative targets may be involved physiologically in vivo, and peptide metabolites may also be involved in providing the pharmaceutically relevant effect. For example, it is known that the analgesic morphine acts by binding to opioid receptors that subsequently modulate calcium and/or potassium channels.

The linear α-conotoxin peptide may be any α-conotoxin peptide which is capable of being cyclised. It may have the sequence of a naturally occurring α-conotoxin peptide, or it may be a derivative thereof. Preferably the α-conotoxin peptide is one which, in its non-cyclised form, has an activity associated with the therapeutic treatment of mammals, such as humans. Since the cyclisation of the peptide has the potential to alter the activity of the peptide, or introduce new activities, it is possible that some cyclised conotoxin peptides may have modified improved therapeutic properties relative to "linear" conotoxins. In some cases the cyclised conotoxin peptide will have a disulfide connectivity different to the linear α-conotoxin peptide, for example Cys I to IV II to III (ribbon) connectivity and Cys I to II, III to IV (beads) connectivity. The peptide may also be presented as a combination of isomers.

According to one embodiment of the invention the linear α-conotoxin peptide which is subject to cyclisation is a 4/7 or 4/6 peptide comprising the sequence set out below:

SEQ ID NO: 1
Xaa$_1$ CCS Xaa$_2$ P Xaa$_3$ C Xaa$_4$ Xaa$_5$ Xaa$_6$ Xaa$_7$ Xaa$_8$
Xaa$_9$ Xaa$_{10}$ C in which Xaa$_1$ is glycine or aspartate, Xaa$_2$ to Xaa$_7$ represent any naturally occurring or unnatural amino acid, Xaa$_8$ represents proline, hydroxyproline, glutamine or serine, Xaa$_9$ represents aspartate, glutamate, γ-carboxyglutamate, glycine or asparagine and Xaa$_{10}$ represents any naturally occurring or unnatural amino acid or may be absent.

More preferably Xaa$_1$ to Xaa$_{10}$ are selected as follows:
Xaa$_1$ is glycine or aspartate,
Xaa$_2$ is selected from aspartate, asparagine, histidine, tyrosine, arginine or lysine, even more preferably from aspartate, asparagine and histidine, and most preferably aspartate,
Xaa$_3$ is selected from arginine, proline, alanine, valine or serine, more preferably arginine, proline or alanine and most preferably arginine,
Xaa$_4$ is selected from asparagine, alanine, arginine, tyrosine, histidine, phenylalanine, serine, isoleucine or lysine, more preferably asparagine, alanine or tyrosine and most preferably asparagine,
Xaa5 is selected from tyrosine, histidine, alanine, valine, glutamine, glycine, luecine, serine, threonine, asparagine, aspartate, glutamate, lysine or arginine, more preferably a hydrophilic amino acid residue, and most preferably tyrosine,
Xaa6 is selected from aspartate, asparagine, serine, threonine glutamate, glycine, arginine or histidine, more preferably aspartate or asparagine, and most preferably aspartate,
Xaa$_7$ is selected from histidine, asparagine or tyrosine, more preferably histidine,
Xaa$_8$ is selected from proline, hydroxyproline, glutamine or serine, more preferably proline,
Xaa$_9$ is selected from glutamate, γ-carboxyglutamate, aspartate, glycine or asparagine, more preferably glutamate, γ-carboxyglutamate and most preferably, glutamate,
Xaa$_{10}$ is selected from isoleucine, tyrosine leucine or des-Xaa$_{10}$, more preferably isoleucine.

In particularly preferred embodiments
Xaa$_1$ is glycine or aspartate,
Xaa$_2$ is aspartate,
Xaa$_3$ is arginine,
Xaa$_4$ is asparagine,
Xaa$_5$ is tyrosine,
Xaa$_6$ is aspartate,
Xaa$_7$ is histidine,
Xaa$_8$ is proline,
Xaa$_9$ is glutamate,
Xaa$_{10}$ is isoleucine.

In a preferred embodiment the linear alpha conotoxin peptide subject to cyclisation is an α4/7 conotoxin peptide. The peptide may have selectivity for particular subtypes of the nAChR. For example the peptide may have selectivity for α3 or α9/α10 subtypes over the α7 subtype of the nAChR.

In a further preferred embodiment the linear alpha conotoxin peptide subjected to cyclisation is Vc1.1.

The cyclised conotoxin peptides according to the present invention will generally consist of an α-conotoxin peptide in which the N- and C-termini are linked via a linking moiety, although in some cases it may be possible to directly connect the N- and C-termini of a naturally occurring α-conotoxin peptide or derivative thereof without the need for an additional linking moiety. The linking moiety, if present, may be a peptide linker such that cyclisation produces an amide-cyclised peptide backbone. These peptides will have no free N- or C-termini.

Considerable variation in the peptide sequence of the linking moiety is possible. Since this linking region does not necessarily bind to or occlude the primary active site of the α-conotoxin it can be modified to alter physiochemical properties, and potentially reduce side effects of the conotoxins.

In linking the N- and C-termini of the conotoxin it may in some cases be necessary or desirable to remove or modify one or more of the N- or C-termini residues. Such modification of the linear conotoxin sequence is within the scope of the present invention. For example, if either the positive or negative charges at the termini of the linear conotoxin were important in activity, then their loss on cyclization could be rescued via substation of amino acids with positive or negative side chains such as lysine or glutamic acid respectively.

The linking moiety will necessarily be of sufficient length to span the distance between the N- and C-termini of the conotoxin peptide. In the case of peptide linkers the length will generally be in the order of 2 to 10 amino acids. In some cases longer or shorter peptide linkers may be required. In one embodiment the linking moiety is composed of glycine and/or alanine residues in addition to any amino acid residues already present in the linear α-conotoxin.

For α-conotoxin peptides of the A-superfamily it has been found that the distance between cysteine residues I and IV is substantially conserved. For such conotoxin peptides, allowing for bond angles and distance, the linker length is preferably chosen such that the number of amino acids between cysteine residue I and IV is between six and eight. Accordingly, for the α-conotoxins Vc1.1 and MII the additional amino acid residues required for the linker would be between five and seven, allowing for the single amino acid already present at the N-terminus.

Accordingly in a further aspect the present invention utilises synthetically cyclised α-conotoxin peptide having an amide cyclised backbone such that the peptide has no free N- or C-terminus, said peptide comprising four cysteine residues bonded in pairs to form two disulfide bonds, wherein the N-terminus of the corresponding linear/non-cyclised conotoxin peptide is linked to the C-terminus by a peptide linker of such that between six and eight amino acid residues span the distance between cysteine residues I and IV.

Preferably the number of amino acids in the linker is selected such that there are seven amino acids between the first and the fourth cysteine residues. Depending on the sequence of the linear peptide, some or all of these residues may be derived from the linear sequence. Accordingly if the conotoxin peptide has one amino acid at the N-terminus adjacent the first cysteine residue, the number of additional amino acids required for the linker would be six.

Of course it would also be possible to substitute one or more of the N-terminal residues with another residue which would form part of the linker.

It is possible, according to the present invention, to modify or potentiate the activity of a conotoxin peptide by selection of a particular size and/or type of peptide linker. Small changes in the conformation of the conotoxin caused by the introduction of a linking group can alter the binding affinities of the peptides for their particular binding sites. Conversely, where the activity is to be as close to the activity of the parent conotoxin peptide as possible, a linker will be selected which minimises any change in conformation.

The linker may also provide a "handle" on the peptide which does not interfere substantially with the primary biological effect. The linker can provide a place for functionalising the molecule to improve biophysical or biopharmaceutical properties, including the ability to cross biological membranes such as might be necessary to provide orally delivered bioactivity.

There are several ways in which linear conotoxins may be cyclised. These include the following:

1. Cyclisation of the Reduced Peptide Followed by Oxidation to Form the Required Disulfide Bonds.

In this approach an extended linear peptide is first synthesised "on resin" using solid phase peptide synthesis methods. This extended linear peptide comprises the native sequence starting at a cysteine residue at, or close to, the N-terminus and a C-terminal extension which comprises the new linking moiety. The solid phase synthesis actually starts in the reverse order—ie at the C-terminus of the extended linear peptide. Following cleavage from the resin, the extended conotoxin is cyclised to a thioester intermediate which subsequently rearranges to an amide-cyclised peptide. This reduced peptide is then oxidised to form the disulfide bonds. A schematic diagram of the reaction involved in the cyclisation is shown in FIG. 1. The linear peptide is cleaved from the resin with the linker to the resin (R) still attached. R corresponds to the linker between the peptide and the resin and is different from the linking moiety used in the cyclisation. The first reaction involves the formation of a thioester between the thiol of the N-terminal cysteine and the carboxy terminus. This then undergoes an S, N acyl migration to form the cyclised peptide with a native peptide bond.

2. Oxidation of the Reduced Linear Peptide, Followed by Cyclisation.

In this approach an extended peptide is assembled using solid phase peptide synthesis. The extended linear peptide comprises the native conotoxin sequence with extra residues added at the N- and/or C-termini. The (new) N and C termini should preferably be glycine residues. The peptide is folded, and in the case of the conotoxin-like peptides, the termini of the folded molecule are generally close together in space. This facilitates the cyclisation of the peptide in solution using standard chemistry. Complications may occur when large numbers of lysine, glutamic acid or aspartic acid residues are present in the sequence and method 1 is then preferable.

3. Ligation of a Linker onto an Existing Conotoxin, Followed by Cyclisation.

In this method the starting material is a mature conotoxin. A peptide linker is synthesised and ligated with the conotoxin using published procedures for the ligation of peptides. The extended peptide is then cyclised and oxidised.

In the process described above the steps can be performed in any order, provided the product is a cyclised α-conotoxin peptide having the required disulfide bonds. For example, in process 1 the cleavage and cyclisation steps may be performed simultaneously or in either order. Similarly in process 2 the cyclisation and folding steps could be performed simultaneously, or in either order.

It is also possible to form the disulfide bonds selectively using protecting groups on the cysteine residues. Selective protection of the cysteine residues in this way allows the production of a particular disulfide bond pattern. Examples of groups capable of protecting cysteine residues include acetamidomethyl (Acm), 4-methylbenzyl (MeBzl) and 4-methoxybenzyl (Mob).

Also, in view of the cyclised nature of the final products, synthetic procedures may involve cyclised permutation of the α-conotoxin peptides or of the extended peptide/linker sequences. For example, the designs of the extended linear peptide for α-conotoxins could commence by adding a linker to the C-terminal residue of the α-conotoxin, cyclically permuting the N-terminal residue(s) to the C-terminal, to provide an N-terminal cysteine, and cyclising as described.

The term "derivative" as used herein in connection with naturally occurring conotoxin peptides, such as MII, refers to a peptide which differs from the naturally occurring peptides by one or more amino acid deletions, additions, substitutions, or side-chain modifications.

Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality, or size, for example Ser↔Thr↔Pro↔Hyp↔Gly↔Ala, Val↔Ile↔Leu, His↔Lys↔Arg, Asn↔Gln↔Asp↔Glu or Phe↔Trp↔Tyr. It is to be understood that some non-conventional amino acids may also be suitable replacements for the naturally occurring amino acids. For example ornithine, homoarginine and dimethyllysine are related to His, Arg and Lys.

Substitutions encompassed by the present invention may also be "non-conservative", in which an amino acid residue which is present in a polypeptide is substituted with an amino acid having different properties, such as a naturally-occurring amino acid from a different group (eg. substituting a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Preferably, amino acid substitutions are conservative.

Additions encompass the addition of one or more naturally occurring or non-conventional amino acid residues. Deletion encompasses the deletion of one or more amino acid residues.

As stated above the present invention includes peptides in which one or more of the amino acids has undergone sidechain modifications. Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of mixed disulfides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulfide bonds. It is also possible to replace the sulphydryl groups of cysteine with selenium equivalents such that the peptide forms a diselenium bond in place of one or more of the disulfide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Proline residues may be modified by, for example, hydroxylation in the 4-position.

A list of some amino acids having modified side chains and other unnatural amino acids is shown in Table 2.

TABLE 2

| Non-conventional amino acid | Code | Non-conventional amino acid | Code |
|---|---|---|---|
| L-α-aminobutyric acid | Abu | L-α-methylhistidine | Mhis |
| α-amino-α-methylbutyrate | Mgabu | L-α-methylisoleucine | Mile |
| aminocyclopropane-carboxylate | Cpro | L-α-methylleucine | Mleu |
|  |  | L-α-methylmethionine | Mmet |
| aminoisobutyric acid | Aib | L-α-methylnorvaline | Mnva |
| aminonorbornyl-carboxylate | Norb | L-α-methylphenylalanine | Mphe |
|  |  | L-α-methylserine | Mser |
| cyclohexylalanine | Chexa | L-α-methyltryptophan | Mtrp |
| cyclopentylalanine | Cpen | L-α-methylvaline | Mval |
| D-alanine | DAla | N-(N-(2,2-diphenylethyl) carbamylmethylglycine | Nnbhm |
| D-arginine | DArg | | |
| D-asparagine | DAsn | 1-carboxy-1-(2,2-diphenyl-ethylamino)cyclopropane | Nmbc |
| D-aspartic acid | DAsp | | |
| D-cysteine | DCys | L-N-methylalanine | Nmala |
| D-glutamine | DGln | L-N-methylarginine | Nmarg |
| D-glutamic acid | DGlu | L-N-methylaspartic acid | Nmasp |
| D-histidine | DHis | L-N-methylcysteine | Nmcys |
| D-isoleucine | DIle | L-N-methylglutamine | Nmgln |
| D-leucine | DLeu | L-N-methylglutamic acid | Nmglu |
| D-lysine | DLys | L-N-methylhistidine | Nmhis |
| D-methionine | DMet | L-N-methylisolleucine | Nmile |
| D-ornithine | DOrn | L-N-methylleucine | Nmleu |
| D-phenylalanine | DPhe | L-N-methyllysine | Nmlys |
| D-proline | DPro | L-N-methylmethionine | Nmmet |
| D-serine | DSer | L-N-methylnorleucine | Nmnle |
| D-threonine | DThr | L-N-methylnorvaline | Nmnva |
| D-tryptophan | DTrp | L-N-methylornithine | Nmorn |
| D-tyrosine | DTyr | L-N-methylphenylalanine | Nmphe |
| D-valine | DVal | L-N-methylproline | Nmpro |
| D-α-methylalanine | DMala | L-N-methylserine | Nmser |
| D-α-methylarginine | DMarg | L-N-methylthreonine | Nmthr |
| D-α-methylasparagine | DMasn | L-N-methyltryptophan | Nmtrp |
| D-α-methylaspartate | DMasp | L-N-methyltyrosine | Nmtyr |
| D-α-methylcysteine | DMcys | L-N-methylvaline | Nmval |
| D-α-methylglutamine | DMgln | L-N-methylethylglycine | Nmetg |
| D-α-methylhistidine | DMhis | L-N-methyl-t-butylglycine | Nmtbug |
| D-α-methylisoleucine | DMile | L-norleucine | Nle |
| D-α-methylleucine | DMleu | L-norvaline | Nva |
| D-α-methyllysine | DMlys | α-methyl-aminoisobutyrate | Maib |
| D-α-methylmethionine | DMmet | α-methyl-γ-aminobutyrate | Mgabu |
| D-α-methylornithine | DMorn | α-methylcyclohexylalanine | Mchexa |
| D-α-methylphenylalanine | DMphe | α-methylcyclopentylalanine | Mcpen |
| D-α-methylproline | DMpro | α-methyl-α-napthylalanine | Manap |
| D-α-methylserine | DMser | α-methylpenicillamine | Mpen |
| D-α-methylthreonine | DMthr | N-(4-aminobutyl)glycine | Nglu |
| D-α-methyltryptophan | DMtrp | N-(2-aminoethyl)glycine | Naeg |
| D-α-methyltyrosine | DMty | N-(3-aminopropyl)glycine | Norn |
| D-α-methylvaline | DMval | N-amino-α-methylbutyrate | Nmaabu |
| D-N-methylalanine | DNmala | α-napthylalanine | Anap |
| D-N-methylarginine | DNmarg | N-benzylglycine | Nphe |
| D-N-methylasparagine | DNmasn | N-(2-carbamylethyl)glycine | Ngln |
| D-N-methylaspartate | DNmasp | N-(carbamylmethyl)glycine | Nasn |
| D-N-methylcysteine | DNmcys | N-(2-carboxyethyl)glycine | Nglu |
| D-N-methylglutamine | DNmgln | N-(carboxymethyl)glycine | Nasp |
| γ-carboxyglutamate | Gla | N-cyclobutylglycine | Ncbut |
| 4-hydroxyproline | Hyp | N-cyclodecylglycine | Ncdec |
| 5-hydroxylysine | Hlys | N-cylcododecylglycine | Ncdod |
| 2-aminobenzoyl (anthraniloyl) | Abz | N-cyclooctylglycine | Ncoct |
|  |  | N-cyclopropylglycine | Ncpro |
| Cyclohexylalanine | Cha | N-cycloundecylglycine | Ncund |
| Phenylglycine | Phg | N-(2,2-diphenylethyl)glycine | Nbhm |
| 4-phenyl-phenylalanine | Bib | N-(3,3-diphenylpropyl)glycine | Nbhe |
| L-Citrulline | Cit | N-(hydroxyethyl)glycine | Nser |
| L-1,2,3,4-tetrahydroiso- | Tic | N-(imidazolylethyl)glycine | Nhis |

TABLE 2-continued

| Non-conventional amino acid | Code | Non-conventional amino acid | Code |
|---|---|---|---|
| quinoline-3-carboxylic acid | | N-(3-indolylyethyl)glycine | Nhtrp |
| L-Pipecolic acid (homo proline) | Pip | N-methyl-γ-aminobutyrate | Nmgabu |
| | | D-N-methylmethionine | Dnmmet |
| L-homoleucine | Hle | N-methylcyclopentylalanine | Nmcpen |
| L-Lysine (dimethyl) | DMK | D-N-methylphenylalanine | Dnmphe |
| L-Naphthylalanine | Nal | D-N-methylproline | Dnmpro |
| L-dimethyldopa or L-dimethoxyphenylalanine | DMD | D-N-methylthreonine | Dnmthr |
| | | N-(1-methylethyl)glycine | Nval |
| L-thiazolidine-4-carboxylic acid | THZ | N-methyla-napthylalanine | Nmanap |
| | | N-methylpenicillamine | Nmpen |
| L-homotyrosine | hTyr | N-(p-hydroxyphenyl)glycine | Nhtyr |
| L-3-pyridylalanine | PYA | N-(thiomethyl)glycine | Ncys |
| L-2-furylalanine | FLA | penicillamine | Pen |
| L-histidine(benzyloxymethyl) | HBO | L-α-methylalanine | Mala |
| L-histidine(3-methyl) | HME | L-α-methylasparagine | Masn |
| D-N-methylglutamate | DNmglu | L-α-methyl-t-butylglycine | Mtbug |
| D-N-methylhistidine | DNmhis | L-methylethylglycine | Metg |
| D-N-methylisoleucine | Dnmile | L-α-methylglutamate | Mglu |
| D-N-methylleucine | DNmleu | L-α-methylhomophenylalanine | Mhphe |
| D-N-methyllysine | DNmlys | N-(2-methylthioethyl)glycine | Nmet |
| N-methylcyclohexylalanine | Nmchexa | L-α-methyllysine | Mlys |
| D-N-methylornithine | DNmorn | L-α-methylnorleucine | Mnle |
| N-methylglycine | Nala | L-α-methylornithine | Morn |
| N-methylaminoisobutyrate | Nmaib | L-α-methylproline | Mpro |
| N-(1-methylpropyl)glycine | Nile | L-α-methylthreonine | Mthr |
| N-(2-methylpropyl)glycine | Nleu | L-α-methyltyrosine | Mtyr |
| D-N-methyltryptophan | DNmtrp | L-N-methylhomophenylalani | Nmhphe |
| D-N-methyltyrosine | DNmtyr | N-(N-(3,3-diphenylpropyl) carbamylmethylglycine | Nnbhe |
| D-N-methylvaline | DNmval | | |
| L-t-butylglycine | Tbug | O-methyl-L-serine | Omser |
| L-ethylglycine | Etg | O-methyl-L-homoserine | Omhser |
| L-homophenylalanine | Hphe | O-methyl-L-tyrosine | MeY |
| L-α-methylarginine | Marg | γ-aminobutyric acid | Gabu |
| L-α-methylaspartate | Masp | O-methyl-L-homotyrosine | Omhtyr |
| L-α-methylcysteine | Mcys | L-Ǝ-homolysine | BHK |
| L-α-methylglutamine | Mgln | L-ornithine | Orn |
| N-cycloheptylglycine | Nchep | N-cyclohexylglycine | Nchex |
| N-(3-guanidinopropyl)glycine | Narg | D-N-methylserine | DNmSer |

These types of modifications may be important to stabilise the peptide if administered to an individual or for use as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

Preferably the cyclised α-conotoxin peptides will retain the Cys residues and characteristic disulfide bonding pattern. Derivatives may include additional Cys residues provided they are protected during formation of the disulfide bonds.

Preferably the conotoxin peptides according to the invention have 12 to 40 amino acids, more preferably 15 to 30.

The cyclised conotoxin peptides according to the present invention are useful as therapeutic agents.

The α-conotoxins bind to nicotinic acetylcholine receptors (nAChRs) which have been implicated in the treatment of pain and in the acceleration of recovery of nerve damage. Such receptors have also been implicated in the pathophysiology of several neuropsychiatric disorders including schizophrenia, depression, addiction, epilepsy, Alzheimer's disease, Parkinson's disease and Tourette's syndrome and thus the α-conotoxins have potential therapeutic indications for these diseases. It is possible that the cyclised α-conotoxin peptide according to the invention target other receptors or ion channels.

The cyclised conotoxin peptides are believed to be particularly useful for the therapeutic treatment or prophylaxis of neuropathic pain. Pain is considered neuropathic if it arises from within the nervous system itself. The involvement of the nervous system can be at various levels: nerves, nerve roots and central pain pathways in the spinal cord and the brain. Neuropathic pain may result from aberrant activity of damaged nerves and is the most difficult form of pain to treat. Neuropathic pain is a form of chronic pain, which is persistently generated and serves no beneficial function for the affected individual. Patients suffering neuropathic pain typically suffer from allodynia (pain from a normally non-painful stimulus) and hyperalgesia (an increased response to a painful stimulus).

There are several, well established animal pain models which demonstrate characteristic pain symptoms of neuropathy, allodynia and hyperalgesia. The chronic constriction injury (CCI) rat model of neuropathic pain involves applying loose ligatures to the sciatic nerve, resulting in inflammation which causes nerve constriction and neuropathy. The partial nerve ligation (PNL) model involves creating a tight ligation around part of the sciatic nerve, leaving the rest of the nerve uninjured and resulting in allodynic and hyperalgesic pain responses. The streptozotocin (STZ) model involves inducing diabetes on pancreatic β cells, resulting in neuropathic pain symptoms such as mechanical hyperalgesia and tactile allodynia.

Assays useful for assessing compounds with the above mentioned activities may be in vitro or in vivo and are known to those skilled in the art. For example, assays useful for assessing activity at nAChRs include those described in WO 00/15654 (Hogg et al., 1999, J. Biol. Chem. 274(51):36559-

64; and Hogg et al., 2003, Reviews of Physiology, Biochemistry and Pharmacology 1:1-46).

Preferably the mammal is in need of such treatment although the peptide may be administered in a prophylactic sense.

As will be readily appreciated by those skilled in the art, the route of administration (oral and enteral) and the nature of the pharmaceutically acceptable vehicle will depend on the nature of the condition and the mammal to be treated. It is believed that the choice of a particular carrier or delivery system, and route of administration, could be readily determined by a person skilled in the art.

In the oral and enteral formulations of the present invention the active peptide may be formulated with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal or sublingual tablets, troches, capsules, elixirs, suspensions, syrups, wafers, and the like. It will be appreciated that some of these oral formulation types, such as buccal and sublingual tablets, have the potential to avoid liver metabolism. However the cyclised peptides of the present invention may also be delivered to the stomach where liver metabolism is likely to be involved. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Liquid formulations may also be administered enterally via a stomach or oesophageal tube.

Enteral formulations may be prepared in the form of suppositories by mixing with appropriate bases, such as emulsifying bases or water-soluble bases. It is also possible, but not necessary, for the cyclised peptides of the present invention to be administered topically, intranasally, intravaginally, intraocularly and the like.

Pharmaceutically acceptable vehicles include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate the oral or enteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically acceptable vehicle. The specification for the novel dosage unit forms of the invention are dictated by and directly dependent on (a) the unique characteristics of the active material and the particular therapeutic effect to be achieved, and (b) the limitations inherent in the art of compounding active materials for the treatment of disease in living subjects having a diseased condition in which bodily health is impaired as herein disclosed in detail.

As mentioned above the principal active ingredient is compounded for convenient and effective administration in effective amounts with a suitable pharmaceutically acceptable vehicle in dosage unit form. A unit dosage form can, for example, contain the principal active compound in amounts ranging from 0.25 μg to about 2000 mg. Expressed in proportions, the active compound is generally present in from about 0.25 μg to about 2000 mg/ml of carrier. In the case of compositions containing supplementary active ingredients, the dosages are determined by reference to the usual dose and manner of administration of the said ingredients.

In some aspects of the invention, administration forms and routes other than oral or enteral are contemplated, for example topical application such as creams, lotions, transdermal patches, sprays and gels, or compositions suitable for inhalation or intranasal delivery, for example solutions or dry powders.

DETAILED DESCRIPTION OF THE INVENTION

The invention will now be described with reference to the accompanying examples and figures which describe the production of some cyclised conotoxin peptides and their biological activity. However, it is to be understood that the particularity of the following description is not to supersede the generality of the preceding description of the invention.

Referring to the figures:

FIG. 1 is a scheme for peptide cyclisation via a C-terminal thioester. The free sulfur of an N-terminal cysteine interacts with the C-terminal thioester to form an intermediate which undergoes an S, N, acyl migration to form a cyclised peptide with a native peptide bond.

FIG. 2 is a representation of the three-dimensional structures of the conotoxins cMII-6 and cMII-7, and includes an overlay of these structures. The disulfide bonds are represented by ball and sticks. The structures were determined by NMR spectroscopy.

FIG. 3 is a graph depicting the concentration-response curves for inhibition of nicotine (5 μM)-evoked catecholamine release from isolated bovine chromaffin cells by increasing concentrations of MII, cMII-5, cMII-6 and cMII-7. The results indicate that the activity of the cyclised peptides is comparable to linear MII.

FIG. 4 is a graph depicting the relative stability of MII, cMII-6 and cMII-7 against attack by proteolytic enzymes as assessed by incubating the peptide with endoproteinase, Endo-GluC. The amount of intact peptide remaining was determined by RP-HPLC.

FIG. 5 is a graph depicting the relative stability of MII, cMII-6 and cMII-7 against enzymes in 50% human plasma. The amount of intact peptide remaining was determined by RP-HPLC.

FIG. 6 is a representation of the three dimensional structures of both Vc1.1 (black) and cyclised Vc1.1-6 (grey). The structures were determined by NMR spectroscopy. The backbones of the twenty lowest energy structures for each peptide are shown overlayed indicating the native conformation of Vc1.1 is retained in cVc1.1-6.

FIG. 7 is a graph depicting the relative biological activity of cVc1.1-6 and Vc1.1, as assessed by measuring catchecholamine release from bovine adrenal chromaffin cells. Chromaffin cells were incubated with indicated amount of peptides for 20 min and then stimulated with 10 µM nicotine for 20 min in the continuing presence of inhibitors. Aliquots were removed and assayed fluorimetrically for catecholamine secretion (n=6 experiments) as previously described (Meunier et al., 2002).

EXAMPLE 1

Cyclised MII Analogues (a) Design and Synthesis

The size of the linker required to span the N and C termini of the native MII peptide was determined using well-known molecular modelling methodology. The three-dimensional model of MII was downloaded from the Protein Data Bank (PDB). The molecular modelling program, Accelrys (Insight II Modeling Environment, Release 2000, San Diego, Accelrys Inc. 2001), was used to determine an appropriate linker length. Briefly, this involved building in an amino acid linker between the N- and C-termini, then locking the conformation of the parent conotoxin structure and performing a simple energy minimisation. The conformation of the parent conotoxin was then unlocked and the entire peptide structure reminimized. Models with a linker size that is too small result in structures with higher energies than those with a linker length that does not perturb the native structure. It was determined that a linker containing a minimum of five residues was required to span the N- and C-termini. Therefore peptides containing linkers of five (GGAAG), six (GGAAGG) and seven (GGAGAAG) residues in addition to the N-terminal glycine were synthesised. This corresponds to a total inter-cysteine length spanning six to eight residues. Distance measurements revealed that each residue in the linker would need to span approximately 2.0 to 2.4 angstroms (note that this is less than an extended conformation which would span approximately 3.5 angstroms and therefore represents a relaxed conformation). Glycines and alanines were chosen for the linker amino acids as they are relatively inert amino acids with small side-chains that are less likely to interact with other residues in the native peptide, or interfere with folding compared to larger or highly functionalised amino acid residues.

(b) Synthesis of Cyclised MII Analogues

The peptides were synthesised using BOC/HBTU chemistry with in situ neutralisation utilising a thioester linker (Schnölzer et al., (1992) Int. J. Pept. Protein Res. 40, 180-193; Dawson et al., (1994) Science 266, 776-9; Tam et al., (1999) J. Am. Chem. Soc. 121, 4316-4324; Yan, L. Z. and Dawson, P. E. (2001) J Am Chem Soc 123, 526-33).

This linker was synthesised by treating Gly PAM resin with 4 equivalents of S-trityl-β-mercaptopropionicacid, 4 equivalents of HBTU and 5 equivalents of DIEA in DMF (2×30 minutes). The trityl group is then removed by treating the resin with TFA/triisopropylsilane/$H_2O$ (96:2:2) for 2×20 minutes. The C-terminal residue of the peptide chain was then added to the linker using standard coupling conditions. Peptides with a C-terminal thioester can also be made using FMOC chemistry by following standard literature procedures [Ingenito, R., Bianchi, E., Fattori, D. and Pessi, A. (1999) J Am Chem Soc 121, 11369-74; Shin, Y., Winans, K. A., Backes, B. J., Kent, S. B. H., Ellman, J. A. and Bertozzi, C. R. (1999) J Am Chem Soc 121, 11684-89; Clippingdale, A. B., Barrow, C. J. and Wade, J. D. (2000) J Pept Sci 6, 225-34; Camarero, J. A., Hackel, B. J., De Yoreo, J. J. and Mitchell, A. R. (2004) J Org Chem 69, 4145-51]. Once the peptide chain was assembled it was cleaved from the resin using HF with cresol and thiocresol as scavengers. The crude peptide mixture was then purified by RP-HPLC utilising a gradient of 0-80% B over 80 minutes (A=0.05% TFA in water, B=90% acetonitrile, 9.95% water, 0.05% TFA) using a $C_{18}$ column. Fractions were collected, analysed by MS and those containing the desired product were pooled and lyophilised.

Oxidation and cyclisation of the purified linear reduced peptide was achieved by dissolving the peptide in either 0.1M $NH_4HCO_3$ (pH 8.1) or 50/50 0.1M $NH_4HCO_3$/iPrOH at a concentration of approximately 0.3 mg/mL. The reaction mixture was stirred overnight at room temperature and the resulting mixture purified by RP-HPLC using the conditions described above. The peptides have the sequence given below.

The six residue linker cyclised MII formed two distinct isomers in an approximate ratio of 45:55. In contrast, the crude oxidation HPLC profile of the five residue linker cyclised MII appeared as a poorly dispersed set of peaks. Finally, the seven residue linker cyclised MII formed one predominant (>90%) isomer which, from the $^1$H NMR data, had a well ordered structure. The small number of peaks in the crude oxidation mixture for the MII analogues with a linker size of six residues (in addition to the N-terminal glycine) provides a preliminary indication that this is the optimal minimal size for MII. For the crude mixtures, individual peaks were collected and analysed by MS. Those containing peptides of a mass corresponding to the cyclised and oxidised peptide were subjected to analytical RP-HPLC. Fractions were then combined based on the HPLC analysis and lyophilised.

The 1D $^1$H NMR spectrum of the cyclised peptides obtained in sufficient amounts were measured. One isomer of the five residue linker peptide appeared to have a well-ordered structure based on the $^1$H NMR spectrum. In the case of the six residue linker peptide the later eluting, more abundant isomer appeared well ordered based on the $^1$H NMR spectrum. The seven residue cyclised MII peptide was also well ordered based on the $^1$H NMR spectrum.

The sequence of the cyclised peptide analogues of MII are shown below:

(a) cMII-5

SEQ ID No. 2

Gly Cys Cys Ser Asn Pro Val Cys His Leu Glu His Ser Asn Leu Cys Gly Gly Ala Ala Gly
|_____|

(b) cMII-6

SEQ ID No. 3

Gly Cys Cys Ser Asn Pro Val Cys His Leu Glu His Ser Asn Leu Cys Gly Gly Ala Ala GlyGly
|_____|

(c) cMII-7

SEQ ID No. 4

Gly Cys Cys Ser Asn Pro Val Cys His Leu Glu His Ser Asn Leu Cys Gly Gly Ala Gly Ala Ala Gly
|_____|

(c) Structural Characterisation of the Cyclised MII Analogues.

Two-dimensional NMR spectral data were then obtained for the three well ordered analogues (now referred to as cMII-5, cMII-6 and cMII-7). A complete NMR assignment was made and the chemical shift of the Hα and $H_N$ protons was compared to those of native MII. A comparison of chemical shift data gives an indication of how similar the structures are. The results revealed that the chemical shifts of cMII-5 were poorly matched to those of MII, indicating a change in structure. In contrast, the chemical shifts of cMII-6 and cMII-7 were highly correlated to those of the native conotoxin. This indicates that cMII-6 and cMII-7 adopt a similar structure to native MII, whereas cMII-5 clearly deviates from the native structure.

From this it was evident, based on the oxidation profile and the NMR data, that a linker of five added residues was too short and interfered with the correct folding of the conotoxin while a linker with six or seven added residues was of sufficient size to allow the cyclised analogue to form a native-like structure. The full three dimensional (3D) structures of both cMII-6 and cMII-7 was determined to confirm the close correlation of structure between the native MII and their cyclised counterparts.

The 3D structure of cMII-6 was determined using NMR spectroscopy. Spectra were obtained on a Bruker DMX 750 spectrometer at 280 and 287 K. The homonuclear spectra recorded included double quantum filtered DQF-COSY [Rance, M., Sørensen, O. W., Bodenhausen, G., Wagner, G., Ernst, R. R. and Wilthrich, K. (1983) Biochem. Biophys. Res. Commun. 117, 479-485.], TOCSY using a MLEV17 spin lock sequence [Bax, A. and Davis, D. G. (1985) J. Magn. Reson. 65, 355-360.] with an isotropic mixing time of 80 ms; ECOSY [Griesinger, C., Sørensen, O. W. and Ernst, R. R. (1987) J. Magn. Reson. 75, 474-492], and NOESY [Jeener, J., Meier, B. H., Bachmann, P. and Ernst, R. R. (1979) J. Chem. Phys. 71, 4546-4553; Kumar, A., Ernst, R. R. and Wuthrich, K. (1980) Biochem. Biophys. Res. Commun. 95, 1-6] with mixing times of 150 and 350 ms. In DQF-COSY and ECOSY experiments, the water resonance was suppressed by low power irradiation during the relaxation delay. For the TOCSY and NOESY experiments, water suppression was achieved using a modified WATERGATE sequence [Piotto, M., Saudek, V. and Sklenar, V. (1992) J. Biomol. NMR 2, 661-665]. Two-dimensional spectra were generally collected over 4096 data points in the f2 dimension and 512 increments in the f1 dimension over a spectral width corresponding to 12 ppm. For identification of slowly exchanging amides, a series of one-dimensional and TOCSY spectra were run immediately after dissolving the sample in $D_2O$. All spectra were processed on a Silicon Graphics workstation using XWINNMR (Bruker). The f1 dimension was zero-filled to 2048 real data points with the f1 and f2 dimensions being multiplied by a sine-squared function shifted by 90° prior to Fourier transformation. Processed spectra were analyzed and assigned using the program XEASY [Eccles, C., Guntert, P., Billeter, M. and Wüthrich, K. (1991) J. Biomol. NMR 1, 111-30]. Spectra were assigned using the sequential assignment protocol [Wüthrich, K. (1986) Wiley-Interscience, New York]. The process was facilitated, in part, using the automatic assignment program NOAH, which is part of the DYANA package [Guntert, P., Mumenthaler, C. and Wüthrich, K. (1997) J. Mol. Biol. 273, 283-98]. Cross-peaks in NOESY spectra recorded in 90% $H_2O$, 10% $D_2O$ with mixing times of 350 and 150 ms were integrated and calibrated in XEASY, and distance constraints were derived using DYANA. Backbone dihedral angle restraints were derived from $^3J_{HNH\alpha}$ coupling constants measured from line shape analysis of antiphase cross-peak splitting in the DQF-COSY spectrum. Angles were restrained to −120°±30° for $^3J_{HNH\alpha}$>8.5 Hz and to −60°±30° for $3J_{HNH\alpha}$<5 Hz. Stereospecific assignments of β-methylene protons and χ1 dihedral angles were derived from $^3J_{\alpha\beta}$ coupling constants, measured from ECOSY spectra, in combination with NOE peak intensities. Preliminary structures were calculated using a torsion angle simulated annealing protocol within DYANA. Final structures were calculated using simulated annealing and energy minimization protocols within CNS version 1.0 [Brünger, A. T., Adams, P. D. and Rice, L. M. (1997) Structure 5, 325-336]. The starting structures were generated using random phi, psi dihedral angles and energy-minimized to produce structures with the correct local geometry. This protocol involves a high temperature phase comprising 4000 steps of 0.015 ps of torsion angle dynamics, a cooling phase with 4000 steps of 0.015 ps of torsion angle dynamics during which the temperature was lowered to 0 K, and finally an energy minimization phase comprising 5000 steps of Powell minimization. Structures were refined using further molecular dynamics and energy minimization in a water shell, as described by Linge and Nilges [Linge, J. P. and Nilges, M. (1999) J. Biomol. NMR 13, 51-9]. The refinement in explicit water involves the following steps. First heating to 500 K via steps of 100 K, each comprising 50 steps of 0.005 ps of Cartesian dynamics. Second, 2500 steps of 0.005 ps of Cartesian dynamics at 500 K before a cooling phase where the temperature was lowered in steps of 100 K, each comprising 2500 steps of 0.005 ps of Cartesian dynamics. Finally, the structures were minimized with 2000 steps of Powell minimization. Structures were analyzed using Promotif and Procheck [Hutchinson, E. G. and Thornton, J. M. (1996) Protein Sci. 5, 212-220; Laskowski, R. A., Rullmannn, J. A., MacArthur, M. W., Kaptein, R. and Thornton, J. M. (1996) J. Biomol. NMR 8, 477-86].

Figure 4:
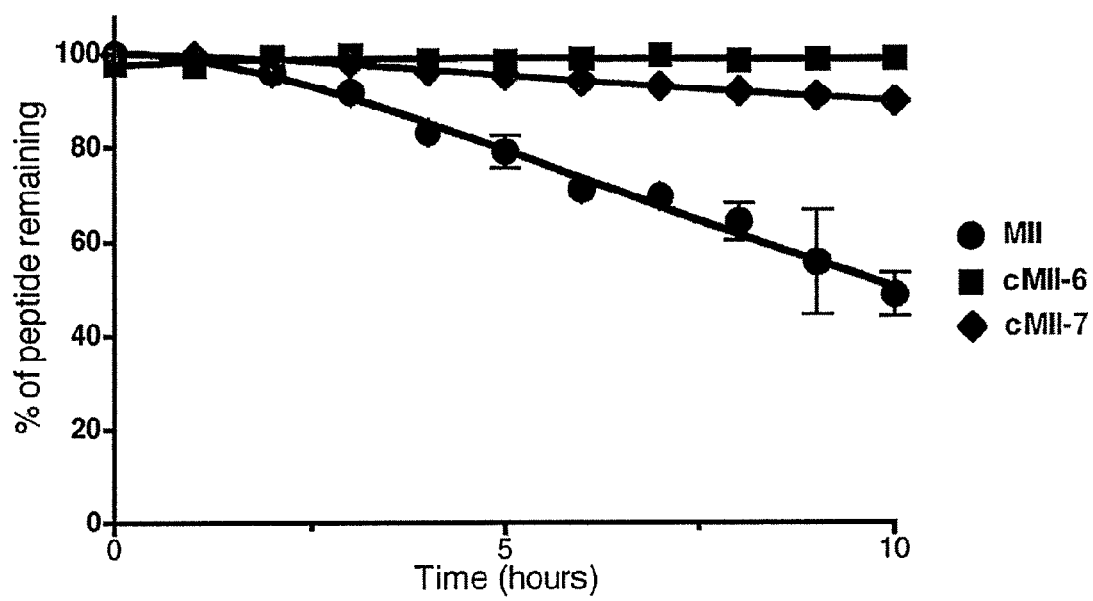

A comparison of cMII-6 with MII show native conformation of MII is retained in toto in cMII-6. The striking degree of similarity between the two peptides is illustrated in FIG. 4.

(d) Selective Synthesis of cMII-6

Although non-selective oxidation is the preferred method used in the synthesis of cyclised conotoxins, they can also be made using directed disulfide bond formation as demonstrated for cMII-6. The peptide was synthesised as described above but the sidechains of cysteines 3 and 16 were protected with Acm groups. The peptide was cleaved from the resin, purified and oxidised/cyclised using the conditions described above. The second disulfide bond was formed selectively between cysteines at positions 3 and 16 by deprotection/oxidation using $I_2$. The peptide (20 mg) was dissolved in 50% aqueous acetic acid at a concentration of 1 mg/mL and the flask flushed with nitrogen. To the flask was added 2 mL of 1M HCl followed by sufficient 0.1M $I_2$ in 50% aqueous acetic acid to make the solution a pale yellow (approximately 1 mL). The reaction was then stirred under nitrogen at room temperature for 1.5 hours. The reaction was quenched by the addition of 1M ascorbic acid until the reaction mixture became colourless. The mixture was then diluted with buffer A and purified by RP-HPLC to yield the cyclised, fully oxidised peptide. This peptide co-eluted with cMII-6 and hence confirmed the disulfide connectivity of cMII-6 as corresponding to that of the native peptide i.e., Cys2-Cys8 and Cys3-Cys16 (1-3, 2-4).

(e) Biological Activity of cMII-6

Figure 1:
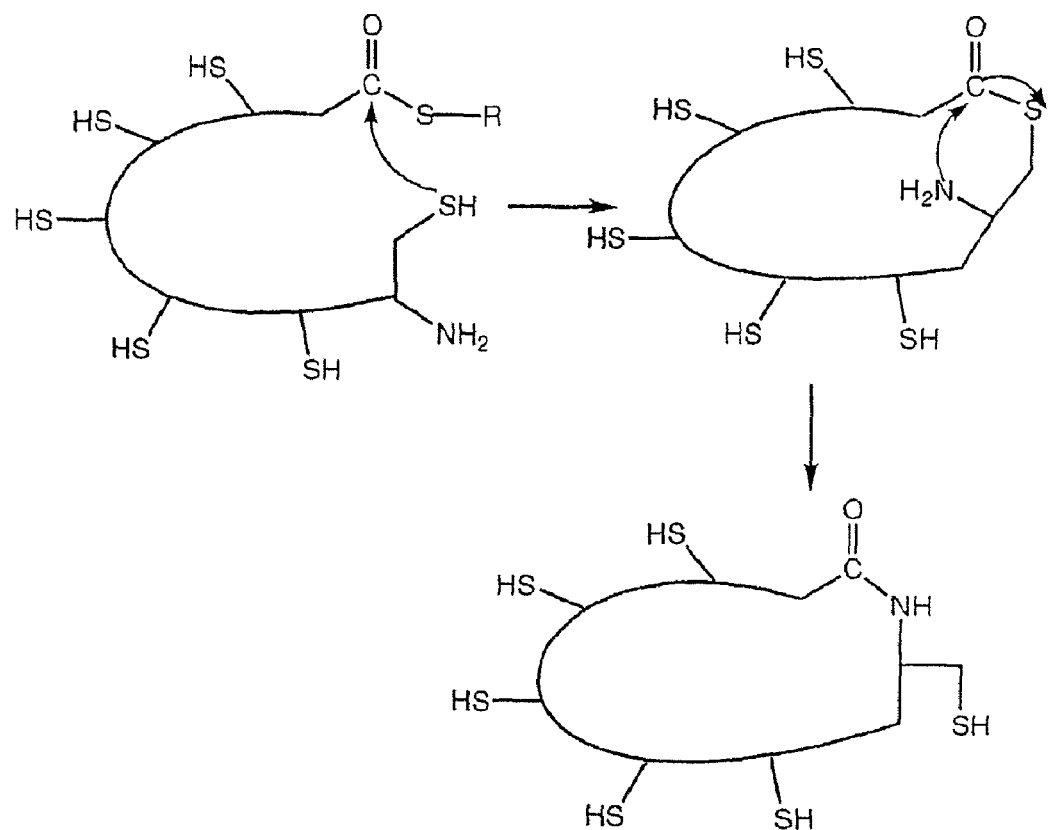
Figure 2:
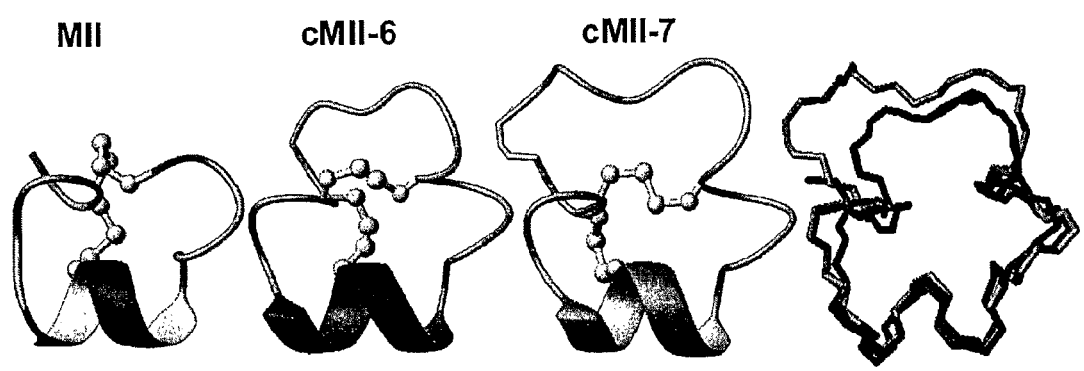
Figure 3:
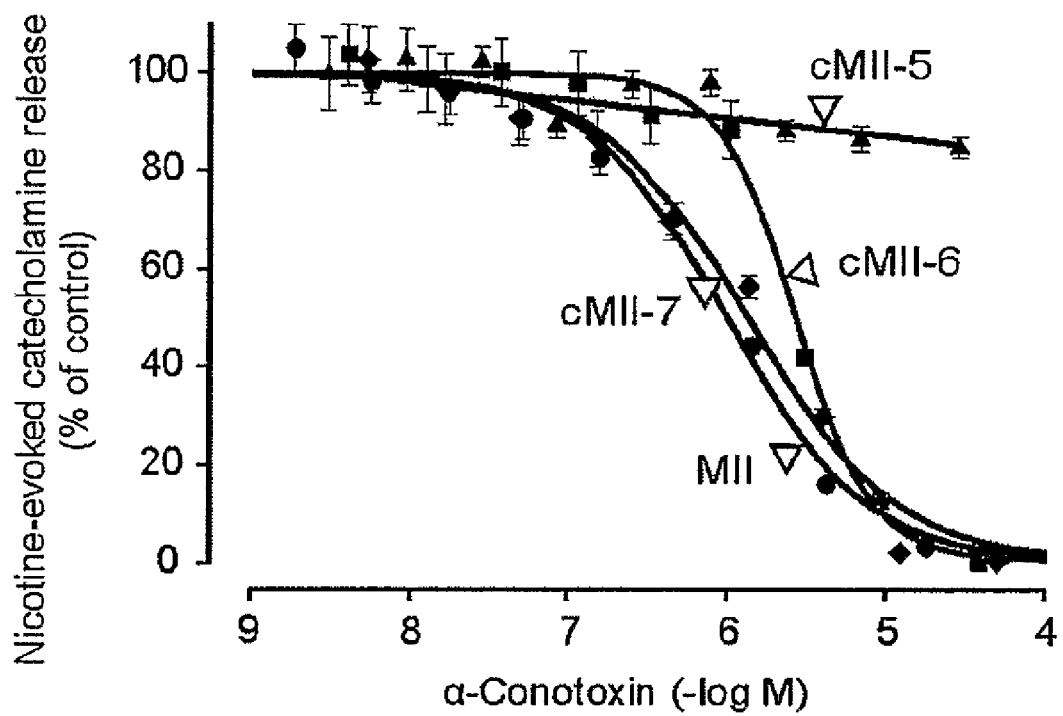

Chromaffin cells were prepared from bovine adrenal glands and maintained in 24-well plates (Nunc) as described in standard literature procedures [Lawrence, G. W., Weller, U. and Dolly, J. O. (1994) Eur J Biochem 222, 325-33; Meunier, F. A., Mattei, C., Chameau, P., Lawrence, G., Colasante, C., Kreger, A. S., Dolly, J. O. and Molgo, J. (2000) J Cell Sci 113 (Pt 7), 1119-25; Meunier, F. A., Feng, Z. P., Molgo, J., Zamponi, G. W. and Schiavo, G. (2002) Embo J 21, 6733-43.]. Intact cells were washed briefly once with buffer A (mM): NaCl, 145; KCl, 5, $Na_2HPO_4$, 1.2; glucose, 10; HEPES-NaOH, 20 (pH 7.4) and incubated with native and cyclised conotoxins for 20 min in the presence of 2 mM $CaCl_2$ and stimulated by nicotine (5 µM) for 20 min. Aliquots of the supernatant were taken at the end of each experiment and cells were lyzed with 1% (v/v) Triton X-100 (Sigma). Both sets of samples were assayed fluorimetrically for catecholamines, and the amount released expressed as a percentage of control as described in the literature (see above). The results of the biological assay are shown in FIG. 3 and indicate that the activity of the cyclised peptides are comparable to that of linear MII.

(f) Stability of cMII-6

The stability of cMII-6 and cMII-7 against attack by proteolytic enzymes was assessed by incubating the peptide with endoproteinase Glu-C (Endo Glu-C). MII, cMII-6 and cMII-7 have an identical potential processing site, on the opposite face from the termini (in MII) and the linker (in cMII-6 and cMII-7). The peptides were dissolved in 0.1M $NH_4HCO_3$ (pH 8.0) buffer at a concentration of 20 µg/mL. Endo GluC was then added at a peptide:enzyme ratio (wt/wt) of 50:1 and the solution incubated at 37° C. Aliquots (3 µL) were taken out and quenched with 5% formic acid (57 µL) every hour from 0-10. Samples were then analysed by LC/MS and the amount of intact peptide remaining at each time point determined. Each trial was performed in triplicate with the appropriate positive (a linear non-disulfide peptide with a EndoGluC cleavage point) and negative (peptide in buffer with no enzyme) controls.

The results of the stability assay are illustrated in FIG. 4. The cyclised peptides remain entirely intact over the full ten hour period whereas native MII has a half life of approximately 10 hours. The enhanced stability demonstrated by cMII-6 and cMII-7 is surprising given that the putative processing sites on MII and the cyclised peptides are identical (ie., on the C-terminal side of Glutamic Acid) and distant from the termini (in MII) and the peptide linker in cMII-6 and cMII-7. Additionally, it may be expected that any enhanced stability would be against only against exoproteases that are active against the N-terminus (MII is amidated at its C-terminus), yet Glu-C is an endoprotease. Thus, the cyclised conotoxins appear to have enhanced stability beyond that which may be expected from protection of the termini alone.

(g) Stability of cMII-6 and cMII-7 Against Enzymes in Human Plasma

To test the resistance of cMII-6 and cMII-7 against proteolytic attack, and compare this with MII these conotoxins were incubated in human blood plasma. MII, cMII-6 and cMII-7 (10 µM) were incubated in 50% human plasma for a period of 24 hours. Aliquots were taken at several time points, quenched with 15% aqueous trichloroacetic acid and centrifuged. The supernatant was then analysed by RP-HPLC.

Figure 5:
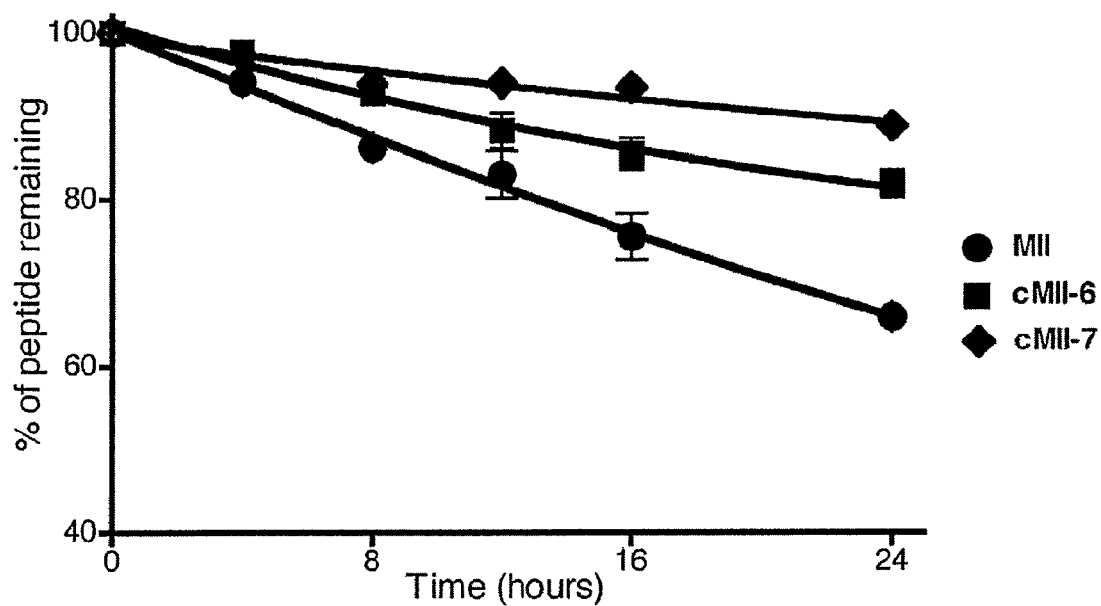

Each trial was performed in triplicate. FIG. 5 shows the results of this experiment. The stability of cMII-6 and cMII-7 is dramatically greater than MII. Native MII had a half-life of approximately 16 hours whereas the amount of cMII-6 and cMII-7 remaining after 24 hours was close to 90%.

EXAMPLE 2

Synthesis and Characterisation of Cyclised Vc1.1

(a) Design of Cyclised Vc1.1

The α-conotoxin Vc1.1 is a member of the 4/7 class of α-conotoxins which includes MII, and has potential for the treatment of pain (Sandall D W, Satkunanathan N, Keays D A, Polidano M A, Liping X, Pham V, Down J G, Khalil Z, Liven B G, Gayler K R, Biochemistry 2003 42(22):6904-11). There was no structural data available for Vc1.1 in the literature and hence the procedure described above for the design of the cyclised MII analogues could not be followed. However, because other conotoxins with this same framework have been studied structurally, the optimal linker length for Vc1.1 was estimated by simple distance measurements on other members of the same family, including MII and PnIA. There are four structures of α4/7 conotoxins in the Protein Data Bank excluding duplicate structures and the conotoxin GID which has an extended flexible "tail" on the N-terminus. By averaging the distance between the N- and C-termini of these structures of these four compounds the value obtained is quite consistent (12.2±0.8 Å). Subsequently, the three dimensional structure of Vc1.1 was reported (Clark et al. J. Biol. Chem. (2006) 281 23254-23263) and revealed that the distance between the N and C termini of Vc1.1 was 11.9±0.5 Å, which falls within this average calculated range for the α4/7 conotoxins. Therefore it can be estimated that suitable linker lengths for cyclising Vc1.1 would be similar to those used for cyclising MII. eg. approximately six to seven residues. Again, these six residues are additional to an existing Glycine residue at the N-terminus.

(b) Synthesis and Structural Characterisation of Cyclised Vc1.1 and Vc1.1

The synthesis of cyclised Vc1.1 was carried out using the synthetic procedures described for cyclised MII (example 1). The cyclisation/oxidation buffer used for cyclised Vc1.1 was 0.1M $NH_4HCO_3$ (pH 8.1). The cyclisation/oxidation yielded one predominant isomer (now referred to as cVc1.1-6) that was purified and analysed by $^1H$ NMR spectroscopy. The sequence of Vc1.1 (which is C-terminally amidated) and cVc1.1-6 are shown below.

SEQ ID NO. 5

Gly Cys Cys Ser Asp Pro Arg Cys Asn Tyr Asp His Pro Glu Ile Cys

SEQ ID NO. 6

Gly Cys Cys Ser Asp Pro Arg Cys Asn Tyr Asp His Pro Glu Ile Cys Gly Gly Ala Ala Gly Gly

Figure 6:
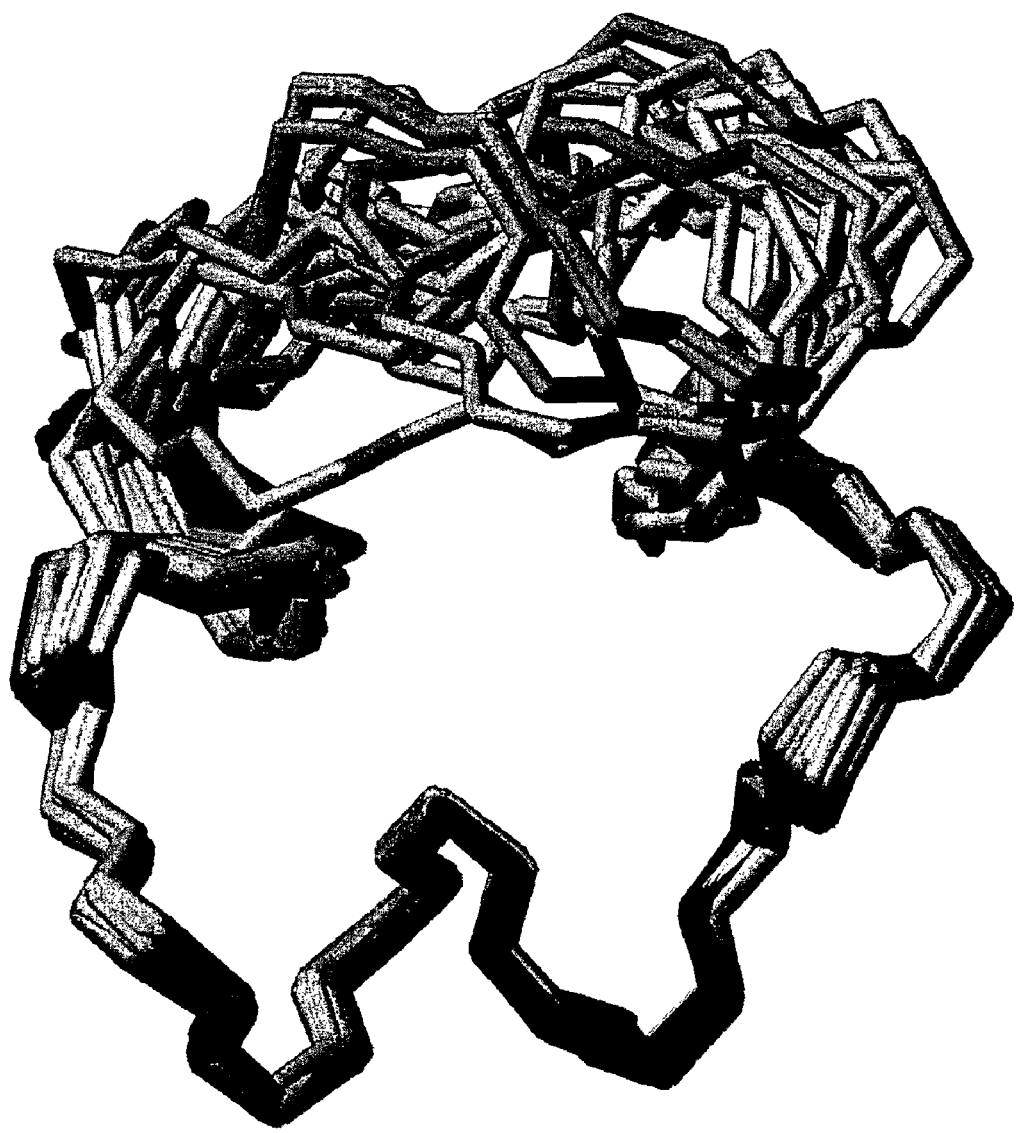

Linear Vc1.1 was also synthesised using BOC/HBTU chemistry with in situ neutralization on MBHA-amide resin. The peptide was folded in 0.1M $NH_4HCO_3$ at room temperature overnight and yielded a single isomer. The disulfide connectivity of synthetic Vc1.1 and cVc1.1-6 were both confirmed to be Cys2-Cys8, Cys3-Cys16 using standard reduction/alkylation methodologies [Göransson, U. and Craik, D. J. (2003) J. Biol. Chem. 278, 48188-96] with MS/MS sequencing. The three dimensional NMR structure was then determined for comparison to cVc1.1-6. The three dimensional structure of both Vc1.1 and cVc1.1-6 was determined using NMR spectroscopy as described above for cyclised MII. The native conformation of Vc1.1 is retained in cVc1.1-6 as shown in FIG. 6.

(c) Disulfide Mapping of Vc1.1

Vc1.1 was partially reduced by incubating with TCEP in citrate buffer at low pH. The reaction mixture was purified by RP-HPLC and the one-disulfide species alkylated with N-ethylmaleimide. The alkylated peptide was then fully reduced and analysed by MS/MS. The M/MS data clearly showed that C2 and C8 had been alkylated with N-ethylmaleimide. Fragmentation patterns from both ends of the peptide chain were observed and fully supported the proposed alkylation pattern. Therefore it was concluded that the disulfide connectivity of Vc1.1 was C2 to C8 and C3 to C16. This is consistent with the I-III, II-IV disulfide bonding pattern seen in other α-conotoxins.

(d) Biological Activity of cVc1.1-6

Figure 7:
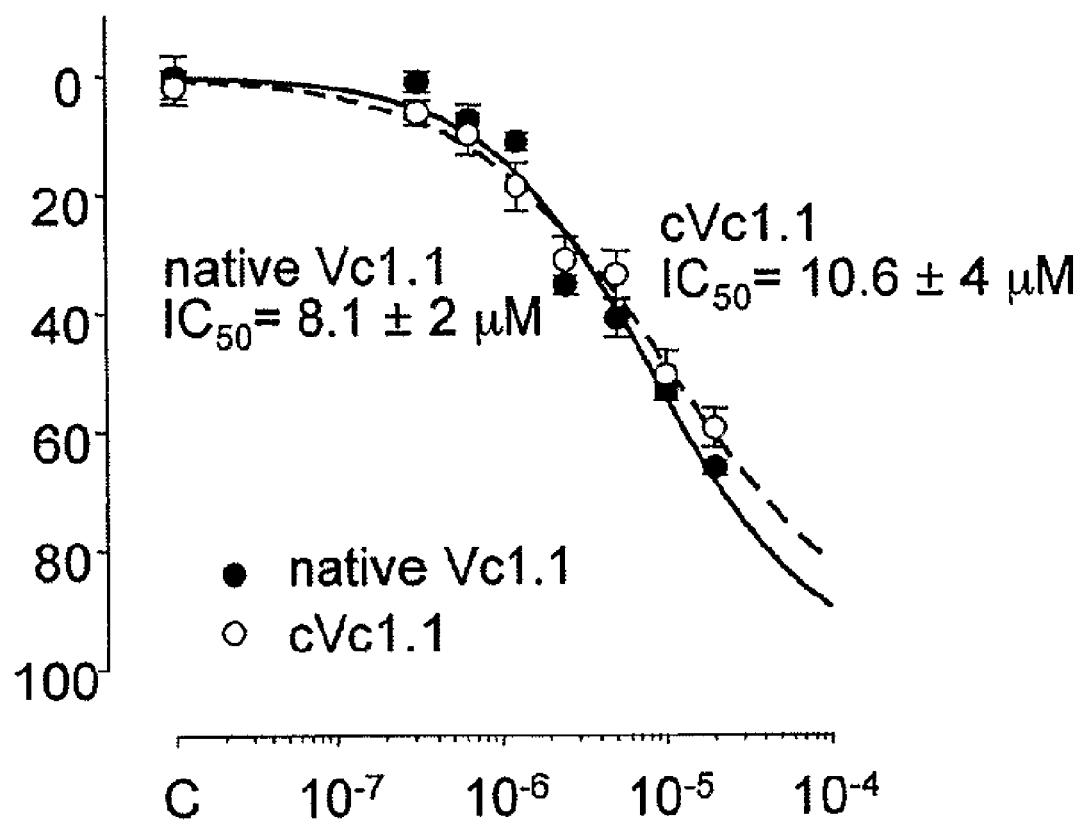

The biological activity of cVc1.1-6 was analysed by measuring catecholamine release from bovine adrenal chromaffin cells as described for the cyclised MII example. The results of the assay are shown in FIG. 7 which demonstrates that the activity of cVc1.1-6 is identical, within experimental error, to that of linear Vc1.1.

(e) Stability of cVc1.1-6

The ability of cVc1.1-6 to resist attack by proteolytic enzymes can be assessed using the experiments outlined for cyclised MII. Resistance to breakdown in mammalian gastric juices and plasma can also be assessed using the protocols given in Example 1.

(f) Selectivity of α-Conotoxin Vc1.1 Inhibition of Recombinant nAChR Subtypes

Vc1.1 inhibition of ACh-induced currents was examined in *Xenopus* oocytes expressing various nAChRs subunit combinations. The ACh-evoked response was assessed every 10 min and the toxin was bath applied 4 mins in prior to co-application of the agonist plus toxin. Vc1.1 (10 μM) failed to inhibit ACh-evoked currents mediated by either the central nAChR subtypes, α4β2 and α4β4, or the skeletal muscle nAChR subtype, αβγδ (n=7–12). Similarly, 10 μM Vc1.1 inhibited only 14±2% of the ACh-evoked current mediated by the homopentameric neuronal nAChR, α7 (n=11). However, 10 μM Vc1.1 inhibited the peripheral nAChR subtypes α3β2 and α3β4 to a similar extent, 58±7% (n=8) and 56±7% (n=12) of control, respectively. A similar potency was observed upon addition of the α5 subunit to the nAChR combination, α3α5β2 (32 (n=7) but Vc1.1 exhibited >5-fold lower potency to inhibit α3α5β4 (n=15). The ACh-induced current amplitude was only inhibited by ~50% by 30 μM Vc1.1 at the α6 containing nAChR subtype, α3α6β2 (n=13). Bath application of Vc1.1 at concentrations of ≦100 nM did not antagonise ACh-evoked currents nor elicit a detectable response alone (ie. >50 nA) for α3-containing nAChRs.

(g) Oral and Subcutaneous Efficacy of cVc1.1-6

A study was undertaken to compare the anti-allodynic (pain-relieving) effect of Vc1.1 and cVc1.1-6 when administered by subcutaneous (s.c.) and oral bolus doses using a well-defined model of neuropathic pain (CCI-rat).

Tactile allodynia, the defining symptom of neuropathic pain, was induced by tying four loose ligatures around the sciatic nerve of the left leg of the rat to induce a chronic constriction injury (CCI) resulting in hypersensitivity to light touch in the hindpaw on the same side (i.e. the ipsilateral hindpaw). Tactile allodynia was assessed using calibrated von Frey filaments involving the application of graded non-noxious pressure to the ipsilateral hindpaw of CCI-rats. In non-injured rats and in the non-injured (contralateral) hindpaw of CCI-rats, the von Frey paw withdrawal threshold (PWT) is ~12 g whereas by 14 days post-CCI surgery, the ipsilateral PWT is ≦6 g. The treatment goal is to alleviate tactile allodynia such that the PWT for the ipsilateral hindpaw is increased from 6 to 12 g.

Figure 8:
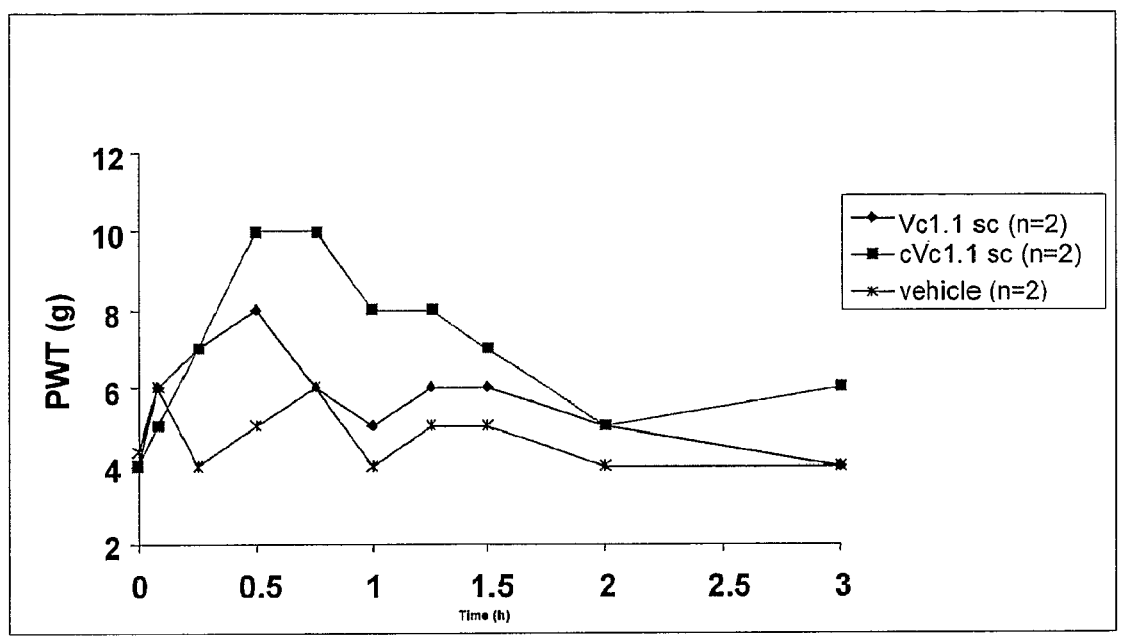
FIG. 8 is a graph depicting increased mean paw withdrawal thresholds (PWTs) in the ipsilateral hindpaw of CCI-rats from <6 g to ~10 g for single bolus s.c. doses of Vc1.1 and cVc1.1-6 (100 µg/kg).
Figure 9:
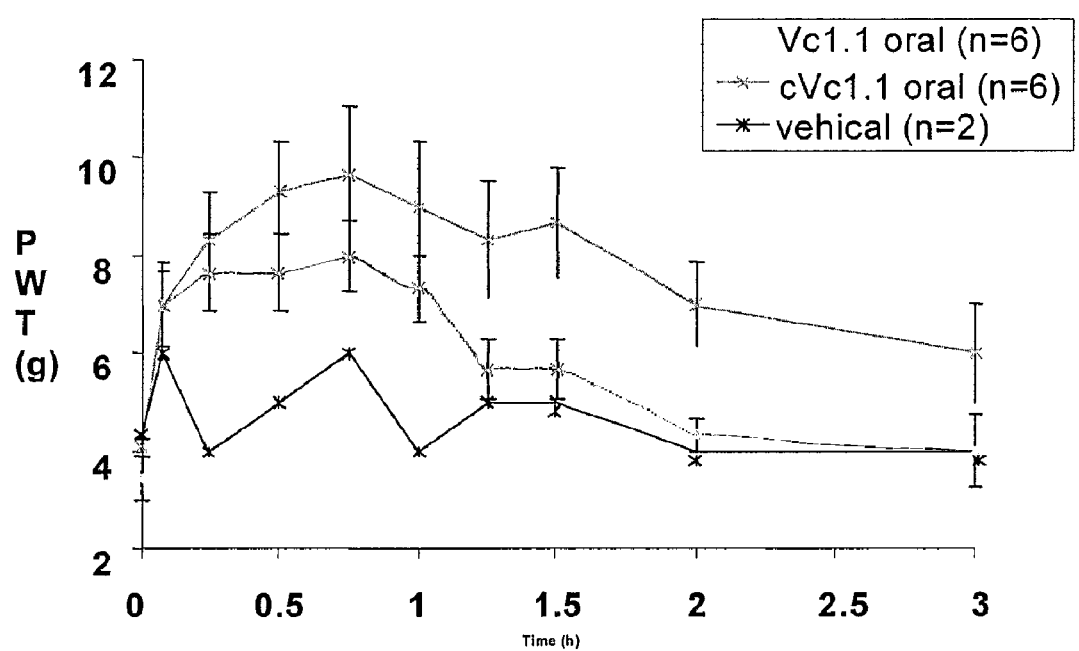
FIG. 9 is a graph depicting increased mean paw withdrawal thresholds (PWTs) in the ipsilateral hindpaw of CCI-rats from <6 g to ~10 g for single bolus oral doses of Vc1.1 and cVc1.1-6 (100 µg/kg).
Figure 10:
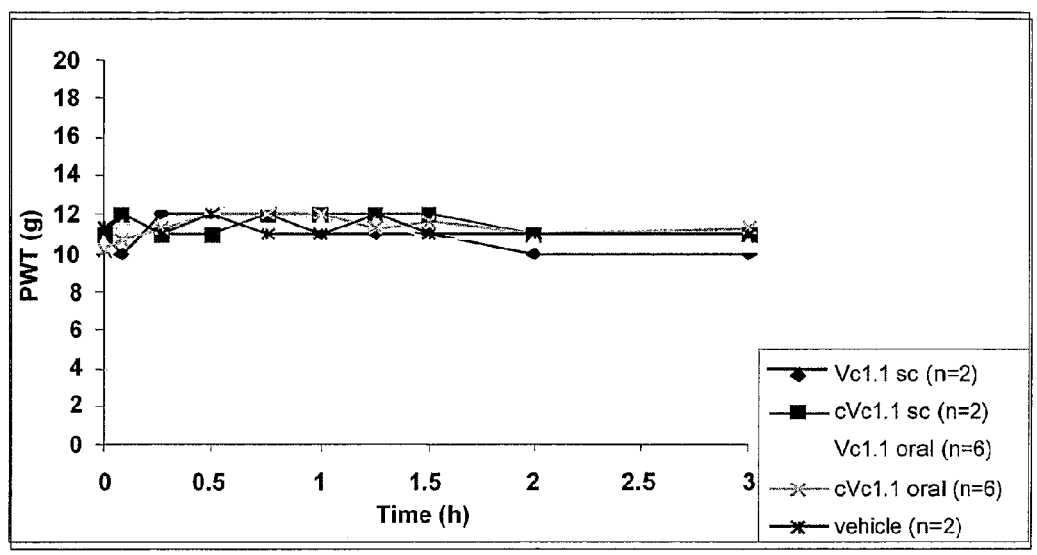
FIG. 10 is a graph depicting mean paw withdrawal thresholds (PWTs) in the contralateral hindpaw of CCI-rats for single bolus s.c. or oral doses of Vc1.1 and cVc1.1-6 (100 µg/kg) in CCI-rats.

Vc1.1 and cVc1.1-6 administered as a single bolus dose (100 μg/kg) by the s.c or the oral route produced significant relief of tactile allodynia as demonstrated by the increase in the mean peak ipsilateral PWT from <6 g to ~10 g. The cyclising of Vc1.1 appeared to result in a longer duration of action compared with the parent linear peptide independent of the route of administration (FIGS. 8 and 9). Neither Vc1.1 nor cVc1.1-6 when administered orally or s.c. increased PWTs in the contralateral hindpaw, consistent with expectations (FIG. 10).

The results demonstrate that cVc1.1-6 was significantly more active than linear Vc1.1 in this in vivo model of neuropathic pain. It also has a longer half life than linear Vc1.1, is more stable, and is orally bioavailable in an animal.

(h) Anti-Allodynic Efficacy and Potency of Cyclised Vc1.1

A study was undertaken to document the anti-allodynic efficacy of single oral bolus doses of cVc1.1-6 in CCI-rats.

Each CCI-rat (n=6) received up to five single oral bolus doses of cVc1.1-6 with a minimum 2-day washout period between doses, in order to identify the effective dose range. Using this approach, effective anti-allodynic doses were between 0.3 mg/kg and 3 mg/kg for cyclised Vc1.1. Larger doses were not tested due to insufficient peptide availability. Control animals received oral bolus doses of vehicle (n=3). The cyclised Vc1.1 or vehicle were administered in a volume of 500 µL using 1 ml Hamilton glass syringes and PWTs were determined utilizing the procedure outlined in 2(h) above.

CCI-rats received a single oral bolus dose of cVc1.1-6 at 1 mg/kg (n=3). Control animals received single oral bolus doses of vehicle (n=3). The cVc1.1-6 or vehicle were administered in a volume of 500 µL using a Hamilton glass syringe and PWTs were determined utilizing the procedure outlined in 2(h).

After completion of the experimental protocol, rats were euthanised with 100% $CO_2$ followed by cervical dislocation. Rat carcasses were frozen until removal by The University of Queensland biological waste removal service.

Figure 12:
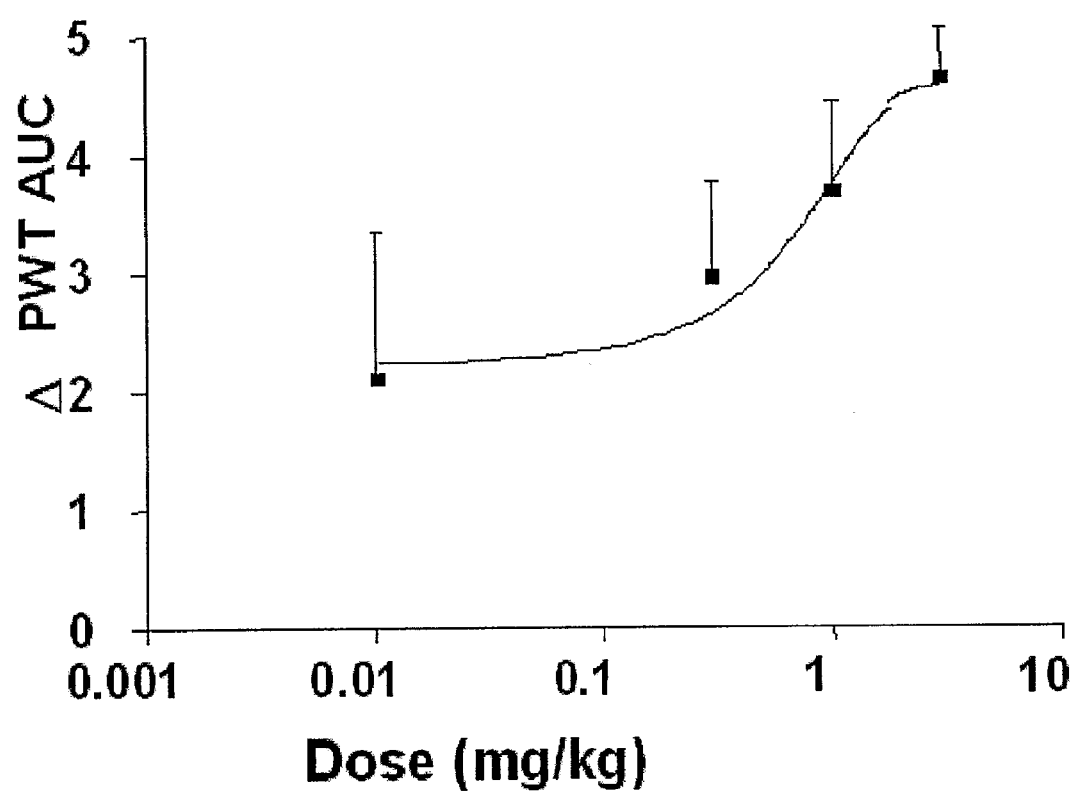
FIG. 12 is a graph depicting the extent and duration of anti-allodynia (ΔPWT AUC values) plotted against dose to produce a dose-response curve; the approximate $ED_{50}$ dose was estimated to be 1 mg/kg.

Mean (±SEM) PWT versus time curves were plotted for each dose of cVc1.1-6 and vehicle in CCI-rats. PWT values were also normalized by subtracting the respective pre-dosing baseline values and the area under the normalized response versus time curves (AUC) were estimated using trapezoidal integration. The AUC values were plotted against dose and the $ED_{50}$ value was estimated (FIG. 12).

As expected, tactile allodynia manifested as a significant (P<0.05) decrease in the mean (±SEM) PWT in the ipsilateral hindpaw (4.8 E 0.2 g) at 21 days post CCI-surgery relative to the respective mean (±SEM) PWT for the contralateral (non-injured) hindpaw (10.6±0.2 g). The treatment target was full reversal of tactile allodynia i.e. von Frey PWTs of ±11 g in the ipsilateral hindpaw.

Figure 11:
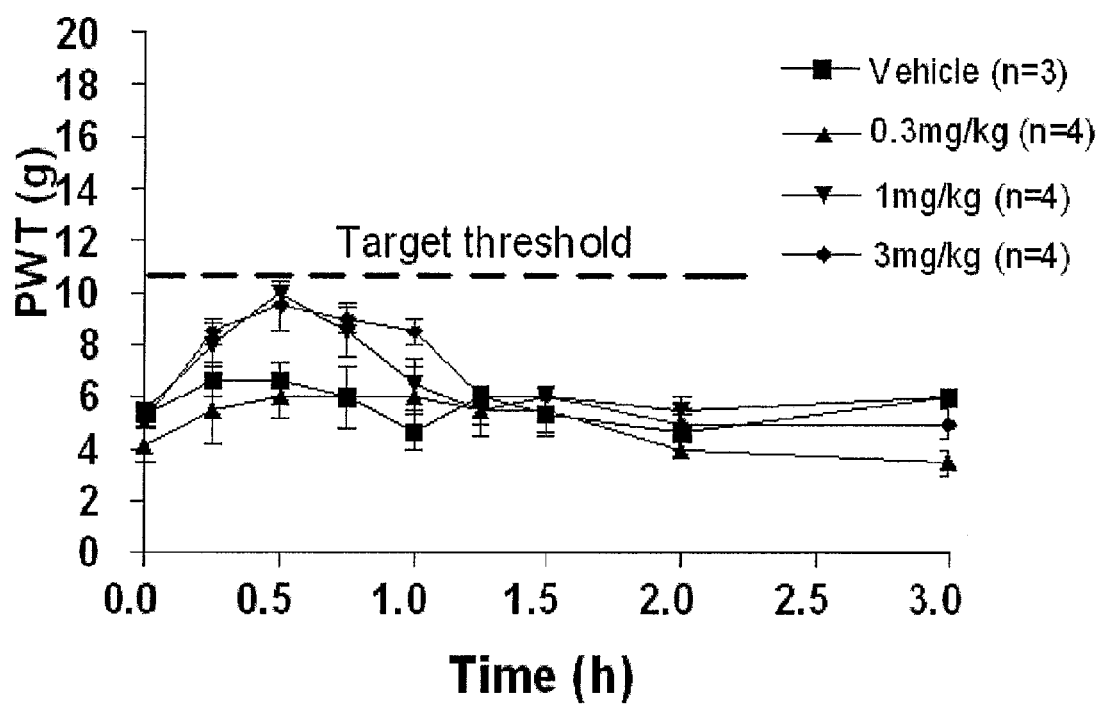
FIG. 11 is a graph depicting mean PWTs for single oral bolus doses of Vc1.1 (0.03-3 mg/kg), which produced dose-dependent relief of tactile allodynia in the ipsilateral hindpaw of CCI-rats.

Following administration of single oral bolus doses of cVc1.1-6 (0.3 to 3 mg/kg) to CCI-rats according to a 'washout' protocol, there was a rapid onset of dose-dependent relief of tactile allodynia in the ipsilateral hindpaw. For all doses tested, peak anti-allodynia in the ipsilateral hindpaw occurred at ~0.5 h post-dosing and the corresponding durations of action were in the range 1-1.25 h. At the highest dose of cVc1.1-6 tested (3 mg/kg), mean (±SEM) PWTs increased from 5.2 (±0.4 g) pre-dose to the peak effect (9.5±1 g) at 0.5 h post-dosing. The mean (±SEM) extent and duration of anti-allodynia (ΔPWT AUC values) in the ipsilateral hindpaw of CCI-rats increased in a dose-dependent manner. The $~ED_{50}$ dose of cVc1.1-6 was estimated at 1 mg/kg and this dose was selected for administration to drug-naïve CCI-rats. Oral administration of cVc1.1-6 in doses up to 3 mg/kg in CCI-rats produced insignificant antinociception in the contralateral hindpaw (FIG. 11).

Following administration of single oral bolus doses of cVc1.1-6 at 1 mg/kg in drug-naïve CCI-rats, there was a rapid onset of relief of tactile allodynia in the ipsilateral hindpaw. Consistent with the findings from the 'washout' protocol, peak anti-allodynia in the ipsilateral hindpaw occurred at ~0.5 h post-dosing and the corresponding mean duration of action was 1.5 h. Specifically, the mean (±SEM) PWT values in the ipsilateral hindpaw of CCI-rats increased from 4 (±0 g) pre-dose to 8.7 (±0.7) g at the time of peak effect (0.5 h). Oral administration of cVc1.1-6 at 1 mg/kg in drug-naïve CCI-rats produced insignificant antinociception in the contralateral hindpaw.

In the study, single oral bolus doses of cVc1.1-6 at the doses tested (0.3-3 mg/kg) did not produce discernible adverse behavioural effects in CCI-rats.

Administration of single oral bolus doses of cVc1.1-6 at 0.3-3 mg/kg in CCI-rats produced dose-dependent anti-allodynic responses in the ipsilateral (injured) hindpaws without producing antinociception in the corresponding contralateral hindpaw. The observation that cVc1.1-6 does not produce antinociception in the contralateral (non-injured) hindpaws is consistent with the notion that cVc1.1-6 produces its pain-relieving effects via modulation of the pro-nociceptive (pro-pain) pathway rather than by amplifying endogenous pain inhibitory mechanisms.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention claimed is:

1. An oral pharmaceutical preparation consisting of:
at least one synthetically cyclised α-conotoxin peptide having an amide cyclised backbone such that the peptide has no free N- or C-terminus, said peptide comprising four cysteine residues bonded in pairs to form two disulfide bonds, one disulfide bond between cysteine residues I and III and one disulfide bond between cysteine residues II and IV,
wherein the N-terminus of the corresponding linear/non-cyclised conotoxin peptide is linked to the C-terminus by a peptide linker, and wherein the corresponding linear/noncyclised α-conotoxin peptide comprises:

SEQ ID NO: 1
Xaa$_1$ CCS Xaa$_2$ P Xaa$_3$ C Xaa$_4$ Xaa$_5$ Xaa$_6$ Xaa$_7$ Xaa$_8$

Xaa$_9$ Xaa$_{10}$ C in which Xaa$_1$ is glycine or aspartate, Xaa$_2$ to Xaa$_7$ represent any naturally occurring or unnatural amino acid, Xaa$_8$ represents proline, hydroxyproline, serine, or glutamine, Xaa$_9$ represents aspartate, glutamate, γ-carboxyglutamate, glycine, or asparagine, and Xaa$_{10}$ represents any naturally occurring or unnatural amino acid or may be absent in a vehicle which is pharmaceutically suitable for oral administration.

2. The pharmaceutical preparation according to claim 1 wherein Xaa$_1$ to Xaa$_{10}$ are selected as follows:
Xaa$_1$ is glycine or aspartate,
Xaa$_2$ is selected from aspartate, asparagine, histidine, tyrosine, arginine or leucine,
Xaa$_3$ is selected from arginine, proline, alanine, valine or serine,
Xaa$_4$ is selected from asparagine, alanine, arginine, tyrosine, histidine, phenylalanine, serine, isoleucine or lysine,
Xaa$_5$ is selected from tyrosine, histidine, alanine, valine, glutamine, glycine, leucine, serine, threonine, asparagine, aspartate, glutamate, lysine or arginine,
Xaa$_6$ is selected from aspartate, asparagine, serine, threonine, glutamate, glycine, arginine or histidine,
Xaa$_7$ is selected from histidine, asparagine or tyrosine,
Xaa$_8$ is selected from proline, hydroxyproline, glutamine or serine,
Xaa$_9$ is selected from glutamate, γ-carboxyglutamate, aspartate, glycine or asparagine, and,
Xaa$_{10}$ is selected from isoleucine, tyrosine, leucine or des-Xaa$_{10}$.

3. The pharmaceutical preparation according to claim 1 wherein Xaa$_1$ to Xaa$_{10}$ are selected as follows:
Xaa$_1$ is glycine or aspartate,
Xaa$_2$ is aspartate,
Xaa$_3$ is arginine,
Xaa$_4$ is asparagine,
Xaa$_5$ is tyrosine,
Xaa$_6$ is aspartate,
Xaa$_7$ is histidine,
Xaa$_8$ is proline,
Xaa$_9$ is glutamate,
and,
Xaa$_{10}$ is isoleucine.

4. The pharmaceutical preparation according to claim 1 wherein the corresponding linear/non-cyclised α-conotoxin peptide is Vc 1.1.

5. The pharmaceutical preparation according to any one of claims 1 to 4 wherein the linker is selected such that there are seven amino acid residues between the first and the fourth cysteine residues.

6. The pharmaceutical preparation according to claim 5 wherein the linker comprises glycine and/or alanine residues in addition to any amino acid residues already present in the linear α-conotoxin.

7. The pharmaceutical preparation according to claim 1 wherein the peptide linker is such that between six and eight natural or unnatural amino acids span the distance between cysteine residues I and IV.

8. The pharmaceutical preparation according to claim 1 wherein the synthetically cyclised peptide is selected from:

Gly Cys Cys Ser Asn Pro Val Cys His Leu Glu His Ser Asn Leu Cys Gly Gly Ala Ala Gly Gly; SEQ ID No. 3

Gly Cys Cys Ser Asn Pro Val Cys His Leu Glu His Ser Asn Leu Cys Gly Gly Ala Gly Ala Ala Gly; SEQ ID No. 4 and,

Gly Cys Cys Ser Asp Pro Arg Cys Asn Tyr Asp His Pro Glu Ile Cys Gly Gly Ala Ala Gly Gly. SEQ ID NO. 6

9. The pharmaceutical preparation according to claim 7 wherein the synthetically cyclised peptide is:

SEQ ID NO. 6

Gly Cys Cys Ser Asp Pro Arg Cys Asn Tyr Asp His Pro Glu Ile Cys Gly Gly Ala Ala Gly Gly.

10. A method for the treatment or prevention of pain comprising the step of orally or enterally administering a pharmaceutical preparation consisting of at least one synthetically cyclised α-conotoxin peptide having an amide cyclised backbone such that the peptide has no free N- or C-terminus, said peptide comprising four cysteine residues bonded in pairs to form two disulfide bonds, one disulfide bond between cysteine residues I and III and one disulfide bond between cysteine residues II and IV, wherein the N-terminus of the corresponding; linear/noncyclised conotoxin peptide is linked to the C-terminus by a peptide linker, and wherein the corresponding linear/noncyclised α-conotoxin peptide comprises:

SEQ ID NO: 1

$Xaa_1$ CCS $Xaa_2$ P $Xaa_3$ C $Xaa_4$ $Xaa_5$ $Xaa_6$ $Xaa_7$ $Xaa_8$ $Xaa_9$ $Xaa_{10}$ C in which $Xaa_1$ is glycine or aspartate, $Xaa_2$ to $Xaa_7$ represent any naturally occurring or unnatural amino acid, $Xaa_8$ represents proline, hydroxyproline, serine, or glutamine, $Xaa_9$ represents aspartate, glutamate, γ-carboxyglutamate, glycine, or asparagine, and $Xaa_{10}$ represents any naturally occurring or unnatural amino acid or may be absent, in a vehicle which is pharmaceutically suitable for oral or enteral administration.

11. The method according to claim 10 wherein the pain is neuropathic pain.

12. The method according to claim 10 wherein the pain is inflammatory pain.

13. The method according to claim 11 wherein the neuropathic pain is diabetic neuropathy pain.

14. A method for accelerating the recovery of nerve damage comprising the step of orally or enterally administering a pharmaceutical preparation consisting of at least one synthetically cyclised α-conotoxin peptide having an amide cyclised backbone such that the peptide has no free N- or C-terminus, said peptide comprising four cysteine residues bonded in pairs to form two disulfide bonds, one disulfide bond between cysteine residues I and III and one disulfide bond between cysteine residues II and IV, wherein the N-terminus of the corresponding; linear/noncyclised conotoxin peptide is linked to the C-terminus by a peptide linker, and wherein the corresponding linear/noncyclised α-conotoxin peptide comprises:

SEQ ID NO: 1

$Xaa_1$ CCS $Xaa_2$ P $Xaa_3$ C $Xaa_4$ $Xaa_5$ $Xaa_6$ $Xaa_7$ $Xaa_8$ $Xaa_9$ $Xaa_{10}$ C in which $Xaa_1$ is glycine or aspartate, $Xaa_2$ to $Xaa_7$ represent any naturally occurring or unnatural amino acid, $Xaa_8$ represents proline, hydroxyproline, serine, or glutamine, $Xaa_9$ represents aspartate, glutamate, γ-carboxyglutamate, glycine, or asparagine, and $Xaa_{10}$ represents any naturally occurring or unnatural amino acid or may be absent, in a vehicle which is pharmaceutically suitable for oral or enteral administration.

15. A method for the treatment of Alzheimer's disease, schizophrenia, depression, epilepsy, small cell lung carcinoma, cardiovascular disorders, gastric motility disorders, urinary incontinence, nicotine addiction, mood disorders or inflammation comprising the step of orally or enterally administering a pharmaceutical preparation consisting of at least one synthetically cyclised αconotoxin peptide having an amide cyclised backbone such that the peptide has no free N- or C-terminus, said peptide comprising four cysteine residues bonded in pairs to form two disulfide bonds, one disulfide bond between cysteine residues I and III and one disulfide bond between cysteine residues II and IV, wherein the N-terminus of the corresponding; linear/noncyclised conotoxin peptide is linked to the C-terminus by a peptide linker, and wherein the corresponding linear/noncyclised α-conotoxin peptide comprises:

SEQ ID NO: 1

$Xaa_1$ CCS $Xaa_2$ P $Xaa_3$ C $Xaa_4$ $Xaa_5$ $Xaa_6$ $Xaa_7$ $Xaa_8$ $Xaa_9$ $Xaa_{10}$ C in which $Xaa_1$ is glycine or aspartate, $Xaa_2$ to $Xaa_7$ represent any naturally or unnatural amino acid, $Xaa_8$ represents proline, hydroxyproline, serine, or glutamine, $Xaa_9$ represents aspartate, glutamate, γ-carboxyglutamate, glycine, or asparagine, and $Xaa_{10}$ represents any naturally occurring or unnatural amino acid or may be absent, in a vehicle which is pharmaceutically suitable for oral or enteral administration.

\* \* \* \* \*

SEQUENCE LISTING

```
<160> NUMBER OF SEQ ID NOS: 45

<210> SEQ ID NO 1
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is glycine or aspartate
<220> FEATURE:
<221> NAME/KEY: MISC_FEATURE
<222> LOCATION: (5)..(5)
<223> OTHER INFORMATION: Xaa can be any naturally occurring or unnatural
      amino acid
<220> FEATURE:
<221> NAME/KEY: MISC_FEATURE
<222> LOCATION: (7)..(7)
```

```
<223> OTHER INFORMATION: Xaa can be any naturally occurring or unnatural
      amino acid
<220> FEATURE:
<221> NAME/KEY: MISC_FEATURE
<222> LOCATION: (9)..(12)
<223> OTHER INFORMATION: Xaa can be any naturally occurring or unnatural
      amino acid
<220> FEATURE:
<221> NAME/KEY: MISC_FEATURE
<222> LOCATION: (13)..(13)
<223> OTHER INFORMATION: Xaa is proline, hydroxyproline, glutamine or
      serine
<220> FEATURE:
<221> NAME/KEY: MISC_FEATURE
<222> LOCATION: (14)..(14)
<223> OTHER INFORMATION: Xaa is aspartate, glutamate, gamma-
      carboxyglutamate, glycine or asparagine
<220> FEATURE:
<221> NAME/KEY: MISC_FEATURE
<222> LOCATION: (15)..(15)
<223> OTHER INFORMATION: Xaa is any naturally occurring or unnatural
      amino acid

<400> SEQUENCE: 1

Xaa Cys Cys Ser Xaa Pro Xaa Cys Xaa Xaa Xaa Xaa Xaa Xaa Xaa Cys
1               5                   10                  15

<210> SEQ ID NO 2
<211> LENGTH: 21
<212> TYPE: PRT
<213> ORGANISM: Artificial Sequence
<220> FEATURE:
<223> OTHER INFORMATION: CMII-5 Synthetic peptide

<400> SEQUENCE: 2

Gly Cys Cys Ser Asn Pro Val Cys His Leu Glu His Ser Asn Leu Cys
1               5                   10                  15

Gly Gly Ala Ala Gly
            20

<210> SEQ ID NO 3
<211> LENGTH: 22
<212> TYPE: PRT
<213> ORGANISM: Artificial Sequence
<220> FEATURE:
<223> OTHER INFORMATION: CMII-6 Synthetic peptide

<400> SEQUENCE: 3

Gly Cys Cys Ser Asn Pro Val Cys His Leu Glu His Ser Asn Leu Cys
1               5                   10                  15

Gly Gly Ala Ala Gly Gly
            20

<210> SEQ ID NO 4
<211> LENGTH: 23
<212> TYPE: PRT
<213> ORGANISM: Artificial Sequence
<220> FEATURE:
<223> OTHER INFORMATION: CMII-7 Synthetic peptide

<400> SEQUENCE: 4

Gly Cys Cys Ser Asn Pro Val Cys His Leu Glu His Ser Asn Leu Cys
1               5                   10                  15

Gly Gly Ala Gly Ala Ala Gly
            20

<210> SEQ ID NO 5
<211> LENGTH: 16
<212> TYPE: PRT
```

<213> ORGANISM: Conus victoriae

<400> SEQUENCE: 5

Gly Cys Cys Ser Asp Pro Arg Cys Asn Tyr Asp His Pro Glu Ile Cys
1 5 10 15

<210> SEQ ID NO 6
<211> LENGTH: 22
<212> TYPE: PRT
<213> ORGANISM: Artificial Sequence
<220> FEATURE:
<223> OTHER INFORMATION: Synthetic construct

<400> SEQUENCE: 6

Gly Cys Cys Ser Asp Pro Arg Cys Asn Tyr Asp His Pro Glu Ile Cys
1 5 10 15

Gly Gly Ala Ala Gly Gly
20

<210> SEQ ID NO 7
<211> LENGTH: 16
<212> TYPE: PRT
<213> ORGANISM: Conus victoriae
<220> FEATURE:
<221> NAME/KEY: MISC_FEATURE
<222> LOCATION: (6)..(6)
<223> OTHER INFORMATION: Xaa represents 4-hydroxy proline
<220> FEATURE:
<221> NAME/KEY: MISC_FEATURE
<222> LOCATION: (14)..(14)
<223> OTHER INFORMATION: Xaa represents gamma-carboxyglutamate

<400> SEQUENCE: 7

Gly Cys Cys Ser Asp Xaa Arg Cys Asn Tyr Asp His Pro Xaa Ile Cys
1 5 10 15

<210> SEQ ID NO 8
<211> LENGTH: 15
<212> TYPE: PRT
<213> ORGANISM: Conus virgo

<400> SEQUENCE: 8

Asp Cys Cys Ser Asn Pro Pro Cys Ala His Asn Asn Pro Asp Cys
1 5 10 15

<210> SEQ ID NO 9
<211> LENGTH: 16
<212> TYPE: PRT
<213> ORGANISM: Conus anemone

<400> SEQUENCE: 9

Gly Cys Cys Ser His Pro Ala Cys Tyr Ala Asn Asn Gln Asp Tyr Cys
1 5 10 15

<210> SEQ ID NO 10
<211> LENGTH: 17
<212> TYPE: PRT
<213> ORGANISM: Artificial Sequence
<220> FEATURE:
<223> OTHER INFORMATION: Synthetic peptide

<400> SEQUENCE: 10

Gly Cys Cys Ser Asp Pro Arg Cys Asn Tyr Asp His Pro Glu Ile Cys
1 5 10 15

Gly

```
<210> SEQ ID NO 11
<211> LENGTH: 17
<212> TYPE: PRT
<213> ORGANISM: Conus sulcatus

<400> SEQUENCE: 11

Gly Gly Cys Cys Ser Tyr Pro Pro Cys Asn Val Ser Tyr Pro Glu Ile
1               5                   10                  15

Cys

<210> SEQ ID NO 12
<211> LENGTH: 16
<212> TYPE: PRT
<213> ORGANISM: Conus distans

<400> SEQUENCE: 12

Gly Cys Cys Ser Asn Pro Pro Cys Ala His Asn Asn Pro Asp Cys Arg
1               5                   10                  15

<210> SEQ ID NO 13
<211> LENGTH: 15
<212> TYPE: PRT
<213> ORGANISM: Conus omaria

<400> SEQUENCE: 13

Gly Cys Cys Ser Tyr Pro Pro Cys Phe Ala Thr Asn Pro Asp Cys
1               5                   10                  15

<210> SEQ ID NO 14
<211> LENGTH: 16
<212> TYPE: PRT
<213> ORGANISM: Conus virgo

<400> SEQUENCE: 14

Asp Cys Cys Ser Asn Pro Pro Cys Ser Gln Asn Asn Pro Asp Cys Met
1               5                   10                  15

<210> SEQ ID NO 15
<211> LENGTH: 16
<212> TYPE: PRT
<213> ORGANISM: Conus virgo

<400> SEQUENCE: 15

Asp Cys Cys Ser Asn Pro Pro Cys Ala His Asn Asn Pro Asp Cys Arg
1               5                   10                  15

<210> SEQ ID NO 16
<211> LENGTH: 16
<212> TYPE: PRT
<213> ORGANISM: Unknown
<220> FEATURE:
<223> OTHER INFORMATION: Unidentified alpha-conotoxin peptide

<400> SEQUENCE: 16

Gly Cys Cys Ser His Pro Ala Cys Ser Val Asn His Pro Glu Leu Cys
1               5                   10                  15

<210> SEQ ID NO 17
<211> LENGTH: 16
<212> TYPE: PRT
<213> ORGANISM: Conus dalli

<400> SEQUENCE: 17

Gly Cys Cys Ser His Pro Ala Cys Asn Val Asp His Pro Glu Ile Cys
1               5                   10                  15
```

```
<210> SEQ ID NO 18
<211> LENGTH: 18
<212> TYPE: PRT
<213> ORGANISM: Conus tulipa

<400> SEQUENCE: 18

Gly Cys Cys Ser His Pro Ala Cys Ser Gly Asn Asn Pro Glu Phe Cys
1               5                   10                  15

Arg Gln

<210> SEQ ID NO 19
<211> LENGTH: 16
<212> TYPE: PRT
<213> ORGANISM: Conus pennaceus

<400> SEQUENCE: 19

Gly Cys Cys Ser His Pro Pro Cys Ala Met Asn Asn Pro Asp Tyr Cys
1               5                   10                  15

<210> SEQ ID NO 20
<211> LENGTH: 20
<212> TYPE: PRT
<213> ORGANISM: Conus circumcisus

<400> SEQUENCE: 20

Gly Cys Cys Ser Asn Pro Val Cys His Val Glu His Pro Glu Leu Cys
1               5                   10                  15

Arg Arg Arg Arg
            20

<210> SEQ ID NO 21
<211> LENGTH: 16
<212> TYPE: PRT
<213> ORGANISM: Conus textile

<400> SEQUENCE: 21

Gly Cys Cys Ser Arg Pro Pro Cys Ile Ala Asn Asn Pro Asp Leu Cys
1               5                   10                  15

<210> SEQ ID NO 22
<211> LENGTH: 17
<212> TYPE: PRT
<213> ORGANISM: Conus betulinus

<400> SEQUENCE: 22

Gly Gly Cys Cys Ser His Pro Ala Cys Ser Val Thr His Pro Glu Leu
1               5                   10                  15

Cys

<210> SEQ ID NO 23
<211> LENGTH: 17
<212> TYPE: PRT
<213> ORGANISM: Conus lividus

<400> SEQUENCE: 23

Glu Asp Cys Cys Ser Asp Pro Arg Cys Ser Val Gly His Gln Asp Leu
1               5                   10                  15

Cys

<210> SEQ ID NO 24
<211> LENGTH: 17
<212> TYPE: PRT
<213> ORGANISM: Conus lividus
```

```
<400> SEQUENCE: 24

Glu Asp Cys Cys Ser Asp Pro Arg Cys Ser Val Gly His Gln Asp Met
1               5                   10                  15

Cys

<210> SEQ ID NO 25
<211> LENGTH: 16
<212> TYPE: PRT
<213> ORGANISM: Conus marmoreus

<400> SEQUENCE: 25

Gly Cys Cys Ser His Pro Ala Cys Ser Val Asn Asn Gln Asp Ile Cys
1               5                   10                  15

<210> SEQ ID NO 26
<211> LENGTH: 16
<212> TYPE: PRT
<213> ORGANISM: Conus obscurus

<400> SEQUENCE: 26

Gly Cys Cys Ser His Pro Pro Cys Ala Gln Asn Asn Gln Asp Tyr Cys
1               5                   10                  15

<210> SEQ ID NO 27
<211> LENGTH: 16
<212> TYPE: PRT
<213> ORGANISM: Conus omaria

<400> SEQUENCE: 27

Gly Cys Cys Ser Asp Pro Ser Cys Asn Val Asn Asn Pro Asp Tyr Cys
1               5                   10                  15

<210> SEQ ID NO 28
<211> LENGTH: 16
<212> TYPE: PRT
<213> ORGANISM: Conus regius

<400> SEQUENCE: 28

Gly Cys Cys Ser His Pro Val Cys Lys Val Arg Tyr Pro Asp Leu Cys
1               5                   10                  15

<210> SEQ ID NO 29
<211> LENGTH: 16
<212> TYPE: PRT
<213> ORGANISM: Conus pennaceus

<400> SEQUENCE: 29

Gly Cys Cys Ser His Pro Pro Cys Phe Leu Asn Asn Pro Asp Tyr Cys
1               5                   10                  15

<210> SEQ ID NO 30
<211> LENGTH: 16
<212> TYPE: PRT
<213> ORGANISM: Unknown
<220> FEATURE:
<223> OTHER INFORMATION: Unidentified alpha-conotoxin peptide

<400> SEQUENCE: 30

Gly Cys Cys Ser Arg Pro Ala Cys Ile Ala Asn Asn Pro Asp Leu Cys
1               5                   10                  15

<210> SEQ ID NO 31
<211> LENGTH: 16
<212> TYPE: PRT
```

<213> ORGANISM: Conus episcopatus

<400> SEQUENCE: 31

Gly Cys Cys Ser Asp Pro Arg Cys Asn Met Asn Asn Pro Asp Tyr Cys
1               5                   10                  15

<210> SEQ ID NO 32
<211> LENGTH: 16
<212> TYPE: PRT
<213> ORGANISM: Conus pennaceus

<400> SEQUENCE: 32

Gly Cys Cys Ser Leu Pro Pro Cys Ala Ala Asn Asn Pro Asp Tyr Cys
1               5                   10                  15

<210> SEQ ID NO 33
<211> LENGTH: 16
<212> TYPE: PRT
<213> ORGANISM: Conus pennaceus

<400> SEQUENCE: 33

Gly Cys Cys Ser Leu Pro Pro Cys Ala Leu Ser Asn Pro Asp Tyr Cys
1               5                   10                  15

<210> SEQ ID NO 34
<211> LENGTH: 16
<212> TYPE: PRT
<213> ORGANISM: Conus aulicus

<400> SEQUENCE: 34

Gly Cys Cys Ser Tyr Pro Pro Cys Phe Ala Thr Asn Ser Asp Tyr Cys
1               5                   10                  15

<210> SEQ ID NO 35
<211> LENGTH: 15
<212> TYPE: PRT
<213> ORGANISM: Conus aulicus

<400> SEQUENCE: 35

Gly Cys Cys Ser Tyr Pro Pro Cys Phe Ala Thr Asn Pro Asp Cys
1               5                   10                  15

<210> SEQ ID NO 36
<211> LENGTH: 16
<212> TYPE: PRT
<213> ORGANISM: Conus aulicus

<400> SEQUENCE: 36

Gly Cys Cys Ser Tyr Pro Pro Cys Phe Ala Thr Asn Ser Gly Tyr Cys
1               5                   10                  15

<210> SEQ ID NO 37
<211> LENGTH: 16
<212> TYPE: PRT
<213> ORGANISM: Conus magus

<400> SEQUENCE: 37

Gly Cys Cys Ser Asn Pro Val Cys His Leu Glu His Ser Asn Leu Cys
1               5                   10                  15

<210> SEQ ID NO 38
<211> LENGTH: 18
<212> TYPE: PRT
<213> ORGANISM: Conus purpurascens

<400> SEQUENCE: 38

Arg Asp Pro Cys Cys Ser Asn Pro Val Cys Thr Val His Asn Pro Gln
1               5                   10                  15

Ile Cys

<210> SEQ ID NO 39
<211> LENGTH: 16
<212> TYPE: PRT
<213> ORGANISM: Conus geographus

<400> SEQUENCE: 39

Gly Cys Cys Ser His Pro Ala Cys Phe Ala Ser Asn Pro Asp Tyr Cys
1               5                   10                  15

<210> SEQ ID NO 40
<211> LENGTH: 19
<212> TYPE: PRT
<213> ORGANISM: Conus geographus
<220> FEATURE:
<221> NAME/KEY: MISC_FEATURE
<222> LOCATION: (4)..(4)
<223> OTHER INFORMATION: Xaa represents gamma-carboxyglutamate
<220> FEATURE:
<221> NAME/KEY: MISC_FEATURE
<222> LOCATION: (16)..(16)
<223> OTHER INFORMATION: Xaa represents 4-hydroxy proline

<400> SEQUENCE: 40

Ile Arg Asp Xaa Cys Cys Ser Asn Pro Ala Cys Arg Val Asn Asn Xaa
1               5                   10                  15

His Val Cys

<210> SEQ ID NO 41
<211> LENGTH: 15
<212> TYPE: PRT
<213> ORGANISM: Conus anemone

<400> SEQUENCE: 41

Cys Cys Ser His Pro Ala Cys Ala Ala Asn Asn Gln Asp Tyr Cys
1               5                   10                  15

<210> SEQ ID NO 42
<211> LENGTH: 17
<212> TYPE: PRT
<213> ORGANISM: Conus anemone

<400> SEQUENCE: 42

Gly Gly Cys Cys Ser His Pro Ala Cys Ala Ala Asn Asn Gln Asp Tyr
1               5                   10                  15

Cys

<210> SEQ ID NO 43
<211> LENGTH: 17
<212> TYPE: PRT
<213> ORGANISM: Conus anemone

<400> SEQUENCE: 43

Gly Gly Cys Cys Ser His Pro Ala Cys Phe Ala Ser Asn Pro Asp Tyr
1               5                   10                  15

Cys

<210> SEQ ID NO 44
<211> LENGTH: 16
<212> TYPE: PRT
<213> ORGANISM: Conus pergrandis

```
<400> SEQUENCE: 44

Gly Cys Cys Ser His Pro Ala Cys Ser Val Asn His Pro Glu Leu Cys
1               5                   10                  15

<210> SEQ ID NO 45
<211> LENGTH: 13
<212> TYPE: PRT
<213> ORGANISM: Conus bullatus

<400> SEQUENCE: 45

Gly Cys Cys Ser Thr Pro Pro Cys Ala Val Leu Tyr Cys
1               5                   10
```